United States Patent
D'Andola et al.

(10) Patent No.: US 8,044,120 B2
(45) Date of Patent: Oct. 25, 2011

(54) IONIC LIQUIDS FOR SOLUBILIZING POLYMERS

(75) Inventors: Giovanni D'Andola, Heidelberg (DE); Laszlo Szarvas, Ludwigshafen (DE); Klemens Massonne, Bad Duerkheim (DE); Veit Stegmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 64 days.

(21) Appl. No.: 12/445,081

(22) PCT Filed: Oct. 12, 2007

(86) PCT No.: PCT/EP2007/060881
§ 371 (c)(1),
(2), (4) Date: Apr. 10, 2009

(87) PCT Pub. No.: WO2008/043837
PCT Pub. Date: Apr. 17, 2008

(65) Prior Publication Data
US 2010/0048829 A1   Feb. 25, 2010

(30) Foreign Application Priority Data
Oct. 13, 2006  (EP) ..................... 06122300

(51) Int. Cl.
*C08G 18/38* (2006.01)
(52) U.S. Cl. ................ 524/35; 524/13; 524/86; 524/87; 524/92; 524/94; 524/98; 524/99; 525/54.21; 525/54.22; 525/403; 525/420; 525/453; 525/537; 162/14; 162/26; 162/29; 162/72; 162/81; 162/91; 162/99; 162/102
(58) Field of Classification Search ............ 162/14, 162/26, 29, 72, 81, 91, 99, 102; 524/13, 524/86, 87, 92, 94, 98, 99, 35; 525/54.21, 525/54.22, 403, 420, 453, 537
See application file for complete search history.

(56) References Cited

U.S. PATENT DOCUMENTS

| | | | |
|---|---|---|---|
| 2007/0193952 A1 | 8/2007 | Maase et al. | |
| 2007/0215300 A1* | 9/2007 | Upfal et al. ............. | 162/29 |
| 2008/0023162 A1 | 1/2008 | Myllymaki et al. | |
| 2008/0058549 A1* | 3/2008 | Jessop et al. .......... | 564/238 |
| 2008/0164440 A1 | 7/2008 | Maase et al. | |
| 2008/0190321 A1 | 8/2008 | Maase et al. | |
| 2008/0269477 A1 | 10/2008 | Stegmann et al. | |
| 2009/0216015 A1* | 8/2009 | Earle et al. ............. | 544/162 |
| 2009/0235574 A1* | 9/2009 | Earle et al. ............. | 44/308 |

FOREIGN PATENT DOCUMENTS

| | | |
|---|---|---|
| DE | 102 02 838 | 8/2003 |
| WO | 03 029329 | 4/2003 |
| WO | 2004 084627 | 10/2004 |
| WO | 2005 007657 | 1/2005 |
| WO | WO 2005/007657 * | 1/2005 |
| WO | 2005 017001 | 2/2005 |
| WO | 2005 017252 | 2/2005 |
| WO | WO 2005/017252 * | 2/2005 |
| WO | 2005 019137 | 3/2005 |
| WO | WO 2006/072785 * | 7/2006 |
| WO | WO 2006/095134 * | 9/2006 |
| WO | 2006 108861 | 10/2006 |
| WO | 2007 057235 | 5/2007 |
| WO | 2007 076979 | 7/2007 |

OTHER PUBLICATIONS

Davis, J.H.; Fox, P.A.; Chemical Communications, 2003, p. 1209-1212.*
U.S. Appl. No. 12/811,100, filed Jun. 29, 2010, Beste, et al.
U.S. Appl. No. 12/523,740, filed Jul. 20, 2009, Balensiefer, et al.
U.S. Appl. No. 12/523,327, filed Jul. 16, 2009, Balensiefer, et al.
U.S. Appl. No. 12/598,9340, filed Nov. 5, 2009, Tishkov, et al.
U.S. Appl. No. 12/747,372, filed Jun. 10, 2010, Degen, et al.

* cited by examiner

*Primary Examiner* — David W Wu
*Assistant Examiner* — Robert Jones, Jr.
(74) *Attorney, Agent, or Firm* — Oblon, Spivak, McClelland, Maier & Neustadt, L.L.P.

(57) ABSTRACT

The present invention relates to a liquid composition which comprises at least one polymer and at least one ionic liquid, the cations of which are derived from polycyclic amidine bases, and a process for isolating cellulose from cellulose-containing sources using at least one such ionic liquid.

15 Claims, No Drawings

IONIC LIQUIDS FOR SOLUBILIZING POLYMERS

The present invention relates to a liquid composition which comprises at least one polymer and at least one ionic liquid, the cations of which are derived from polycyclic amidine bases, and a process for isolating cellulose from cellulose-containing sources using at least one such ionic liquid.

A main problem in providing liquid polymer compositions is the low water-solubility of many polymers. It has an adverse effect, in particular, if these must already be necessarily solubilized to obtain them. Thus e.g. many biopolymers are obtained from natural sources by liquid extraction or must be dissolved for their purification. Solubilization of a polymer must furthermore often be relied upon in order to be able to subject it to a chemical or physical modification. Recycling of various polymers also comprises solubilization as an essential step in order to be able to separate off and recover the polymer from other components.

Cellulose is a raw material which has very diverse uses. For the textile industry, cellulose is, for example, the most important constituent of fiber raw materials, in particular cotton. With a content of about 700 thousand million tonnes of the estimated biomass reserve of 1.5 billion tonnes on the earth, cellulose is the most important representative in the group of organic biopolymers. Pulp which is obtained from wood and cotton, and which has a very high content of cellulose, is currently the most important raw material base for the production of paper, cardboard and regenerated cellulose fibers and film. Cellulose can be employed in unchanged form or after physical or chemical treatment. For the last two cases mentioned, it is of advantage here if cellulose is in a form dissolved as completely as possible in a solvent. However, cellulose is insoluble in most solvents.

In the past, some solvent systems have been developed for processing cellulose. The viscose process, which has already been known for a long time, is currently still of the greatest industrial importance. In this, cellulose is first derivatized to xanthogenate, and then dissolved in dilute sodium hydroxide solution. The derivatization is reversed by regeneration in special coagulation baths, and cellulose is made available in this way. Nevertheless, large amounts of salts and sulfur-containing waste gases are formed due to the process, and must be treated with the aid of preserving technologies. In some copper solutions, cellulose is soluble as a copper-chelate complex. So-called regenerated cellulose can be obtained by precipitation of the cellulose. However, such copper solutions are not particularly suitable as solvents for cellulose during its physical or chemical treatment.

In the wake of the increasing environmental awareness of the last decades, developments have been forced for direct dissolving of cellulose with a lower unavoidable production of waste products and undesirable emissions. The process with the solvent N-methylmorpholine-N-oxide-monohydrate (NMMO) has currently acquired the most important industrial significance here. Disadvantages in this context are the narrow solution window in the ternary system of NMMO, water and cellulose, the use of an oxidizing solvent and the system-related fibrillation of the products produced.

A further problem which has not yet been satisfactorily solved industrially is the obtaining of cellulose from lignocellulose-containing sources, such as wood, with the cellulose being separated off as completely as possible in a high purity. Various processes are known for the removal of lignin (delignification) from lignin-containing sources of cellulose. In the Kraft process, the cellulose is separated off by boiling lignocellulose material, e.g. wood chips, in an alkaline sulfur salt solution. A brown cellulose is obtained, which necessitates subsequent bleaching with chlorine or oxygen. In the sulfite process, the lignin is boiled in an acid sulfur salt solution and separated off. The pulp obtained from the sulfite process is lighter-colored and softer, but not so firm. Only half the wood is processed in these two processes. The other half is burned and used to produce energy. These processes lead to a considerable load on the environment. More recent processes for obtaining pulp (e.g. the all-cell process or the organocell process) dissolve the concomitant lignins out of the wood with the aid of organic solvents at elevated temperature and pressure. This results in the problem of recycling of the organic (readily volatile) solvents employed.

Ionic liquids are gaining increasing importance as solvents, e.g. for carrying out chemical reactions. Peter Wasserscheidt, Angew. Chem. 2000, 112, 3926-3945, for example, gives an overview of the use of ionic liquids in transition metal catalysis.

Ionic liquids which are already in the liquid state of aggregation at room temperature are described, for example, by K. N. Marsh et al., Fluid Phase Equilibria 219 (2004), 93-98 and J. G. Huddleston et al., Green Chemistry 2001, 3, 156-164.

DE-A 102 02 838 describes the use of ionic liquids for separating off acids from chemical mixtures. WO 2005/019137 describes a process for extraction of impurities with ionic liquids.

WO 2006/108861 discloses a solution comprising cellulose, an ionic liquid containing anions and cations as solvent and 6 to 30 wt. % of a nitrogenous base, based on the total weight of the solution.

WO 2007/057235 discloses a solution containing cellulose and an ionic liquid containing anions and cations as a solvent, the cations being provided with at least one atom selected among the group comprising nitrogen, oxygen, sulfur, and phosphorus supplied in a protonated form.

WO 2007/076979 describes a solvent system for biopolymers in the form of carbohydrates which is based on a molten ionic liquid, with additives being present in the solvent system if appropriate.

WO 2005/007657 describes the use of salts of 1,5-diazabicyclo[4.3.0]non-5-ene (DBN) and 1,8-diazabicyclo[5.4.0]undec-7-ene (DBU) which are liquid at temperatures below 35° C. and 760 mm Hg or of other salts which are liquid at temperatures below 35° C. and 760 mm Hg, inter alia formed from saturated, cyclic amines having 1, 2 or more nitrogen atoms as ionic liquids. A use for solubilizing polymers and specifically cellulose is not described.

On the basis of the good solvent properties of ionic liquids, the use thereof for dissolving cellulose is also proposed in the more recent international application WO-A 03/029329. In this, however, it is emphasized that a solution in this respect of cellulose and an ionic liquid as the solvent should contain substantially no nitrogen-containing bases.

WO 2004/084627 describes a process for the preparation of capsules of regenerated cellulose with an active constituent, in which an ionic liquid is used as the solvent. The cations of the ionic liquid are derived from various cyclic amine bases, pyridinium, pyridazinium, pyrimidinium, pyrazinium, imidazolium, pyrazolium, oxazolium, 1,2,3- and 1,2,4-triazolium, thiazolium, piperidinium, pyrrolidinium, quinolinium and isoquinolinium being mentioned concretely.

WO 2005/017001 describes a process for dissolving a lignocellulose material with an ionic liquid under microwave irradiation and/or pressure and in the absence of water. The cations of the ionic liquid correspond to those mentioned in WO 2004/084627.

WO 2005/017252 describes a process for treatment of a lignocellulose material with an ionic liquid, e.g. for delignification. The use of ionic liquids, the cations of which are derived from polycyclic amine bases, is not described.

There continues to be a need for ionic liquids for solubilization of various polymers. Specifically, there is a need for ionic liquids which are suitable for treatment of lignocellulose materials to obtain a product enriched in cellulose. The obtaining of cellulose from lignin-containing sources, such as wood, with the cellulose being separated off as completely as possible in a high purity should be rendered possible by this means. The ionic liquids employed should moreover be as easy as possible to recycle.

The object is achieved, surprisingly, by an ionic liquid, the cations of which are derived from polycyclic amidine bases.

The invention therefore first relates to a liquid composition comprising at least one ionic liquid of the general formula I

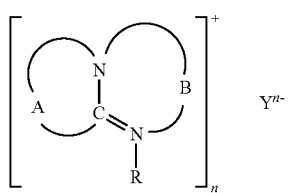

wherein

A together with the C—N group to which it is bonded, forms a 4- to 8-membered, saturated or unsaturated or aromatic ring, which is optionally substituted and/or which can optionally contain further heteroatoms or heteroatom-containing groups and/or which can include further fused-on saturated, unsaturated or aromatic carbocyclic rings or heterocyclic rings, B together with the amidino group to which it is bonded, forms a 4- to 8-membered, mono- or polyunsaturated, non-aromatic ring, which is optionally substituted and can include further fused-on saturated, unsaturated or aromatic carbocyclic rings or heterocyclic rings, R represents hydrogen or an organyl radical, $Y^{n-}$ represents a mono-, di-, tri- or tetravalent anion, and n represents one, two, three or four, and at least one polymer solubilized therein.

The cation in the formula I represents a mesomeric resonance structure. Those cations which result from a delocalization of the positive charge from the protonated or alkylated nitrogen atom via at least a part of the remaining molecule are also included. In this context, however, the bridging group B does not form an aromatic ring with the amidino group to which it is bonded.

Cations and anions are present in the ionic liquid. In this context, within the ionic liquid, a proton or an alkyl radical can be transferred from the cation to the anion, whereby two neutral molecules result. An equilibrium of anions, cations and neutral molecules can therefore be present in the ionic liquid employed according to the invention.

The ionic liquids employed according to the invention are advantageously suitable for solubilizing polymers, and specifically polysaccharides and polyurethanes.

In the context of the present application, the term "solubilization" is understood broadly, and means quite generally conversion into a flowable state. In this context, the term "solubilization" includes the provision of solutions of the polymers and also conversion into a solubilized state which differs therefrom.

If a polymer is converted into a solubilized state, the individual polymer molecules do not necessarily have to be completely surrounded by a solvate shell. It is essential that the polymer is converted into a liquid state by the solubilization. In this context, solubilization using ionic liquids is in general achieved without considerable heating. In the context of the invention, this is understood as meaning that temperatures of preferably not more than 200° C., preferably not more than 150° C., particularly preferably not more than 120° C. and especially not more than 100° C. are employed for the solubilization.

In the context of the present invention, the expression "alkyl" includes straight-chain or branched alkyl. It is preferably straight-chain or branched $C_1$-$C_{30}$-alkyl, in particular $C_1$-$C_{20}$-alkyl and very particularly preferably $C_1$-$C_{12}$-alkyl. Examples of alkyl groups are, in particular, methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The expression alkyl also includes alkyl radicals in which the carbon chains can be interrupted by one or more non-adjacent groups which are chosen from —O—, —S—, —$NR^e$—, —CO— and/or —$SO_2$—. $R^e$ preferably represents hydrogen, alkyl, cycloalkyl, hetero-cycloalkyl, aryl or hetaryl.

Examples of alkyl radicals in which the carbon chains can be interrupted by one or more non-adjacent groups are the following:

2-methoxyethyl, 2-ethoxyethyl, 2-propoxyethyl, 2-butoxyethyl, 3-methoxypropyl, 3-ethoxypropyl, 3-propoxypropyl, 3-butoxypropyl, 4-methoxybutyl, 4-ethoxybutyl, 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9trioxaundecyl, 3,6,9-trioxadodecyl, 3,6,9,12-tetraoxamidecyl and 3,6,9,12-tetraoxatetradecyl;

2-methylthioethyl, 2-ethylthioethyl, 2-propylthioethyl, 2-butylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl.

Examples of alkyl radicals in which the carbon chains can be interrupted by several non-adjacent groups are also polyoxyalkylenes, i.e. compounds with recurring units, which are preferably chosen from $(CH_2CH_2O)_{x1}$, $(CH(CH_3)CH_2O)_{x2}$ and $((CH_2)_4O)_{x3}$, wherein x1, x2 and x3 independently of one another represent an integer from 2 to 100, preferably 3 to 80. The sum of x1, x2 and x3 represents an integer from 2 to 300, preferably 3 to 100. In polyoxyalkylenes which contain two or three different recurring units, the sequence is as desired, i.e. they can be statistically distributed, alternating or block-like recurring units. The above statements for the polyoxyalkylenes apply analogously to polyalkyleneimines, wherein the oxygen atom is in each case replaced by an $NR^e$ group, wherein $R^e$ preferably represents hydrogen or $C_1$-$C_4$-alkyl.

The expression alkyl also includes substituted alkyl radicals. Substituted alkyl groups can contain one or more (e.g. 1, 2, 3, 4, 5 or more than 5) substituents, depending on the length of the alkyl chain. These are preferably chosen independently of one another from cycloalkyl, heterocycloalkyl, aryl, hetaryl, halogen, hydroxyl, SH, COOH, carboxylate, $SO_3H$, sulfonate, $NE^1E^2$, nitro and cyano, wherein $E^1$ and $E^2$ independently of one another represent hydrogen, alkyl, cycloalkyl, heterocycloalkyl, aryl or hetaryl. Carboxylate and sulfonate represent a derivative of a carboxylic acid function or of a sulfonic acid function, in particular a metal carboxylate or sulfonate, a carboxylic acid ester or sulfonic acid ester or a carboxylic acid amide or sulfonic acid amide. Cycloalkyl, heterocycloalkyl, aryl and hetaryl substituents of the alkyl groups can in their turn be unsubstituted or substituted; suitable substituents are those mentioned below for these groups.

The above statements relating to alkyl also apply to the alkyl moieties in alkoxy, alkylamino, alkylthio (alkylsulfanyl), alkylsulfinyl, alkylsulfonyl, etc.

Suitable substituted alkyl radicals are the following:
carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;
sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;
2-hydroxyethyl, 2- and 3-hydroxypropyl, 3- and 4-hydroxybutyl and 8-hydroxy-4-oxaoctyl;
2-cyanoethyl, 3-cyanopropyl, 3- and 4-cyanobutyl;
2-chloroethyl, 2- and 3-chloropropyl, 2-, 3- and 4-chlorobutyl, 2-bromoethyl, 2- and 3-bromopropyl and 2-, 3- and 4-bromobutyl;
2-nitroethyl, 2- and 3-nitropropyl and 2-, 3- and 4-nitrobutyl.

Examples of alkoxy are: methoxy, ethoxy, propoxy, butoxy, pentoxy and hexoxy;

Examples of alkylthio are methylthio, ethylthio, propylthio, butylthio, pentylthio and hexylthio.

Alkyl radicals substituted by aryl ("arylalkyl") contain at least one, as defined below, unsubstituted or substituted aryl group. In this context, the alkyl group in "arylalkyl" can carry at least one further substituent and/or be interrupted by one or more non-adjacent groups which are chosen from —O—, —S—, —$NR^{e-}$, —CO— and/or —$SO_2$—. $R^e$ preferably represents hydrogen, alkyl, cycloalkyl, heterocycloalkyl, aryl or hetaryl. Arylalkyl preferably represents phenyl-$C_1$-$C_{10}$-alkyl, particularly preferably phenyl-$C_1$-$C_4$-alkyl, e.g. benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(benzyl)-eth-1-yl, 1-(benzyl)-1-(methyl)-eth-1-yl or 1-(benzyl)-1-(methyl)-prop-1-yl; preferably benzyl and 2-phenylethyl.

In the context of the present invention, the expression "alkenyl" includes straight-chain and branched alkenyl groups, which can carry one or more double bonds (e.g. 1, 2, 3, 4 or more than 4), depending on the chain length. Preferred groups are $C_2$-$C_{18}$—, particularly preferably $C_2$-$C_{12}$-alkenyl groups. The expression "alkenyl" also includes substituted alkenyl groups, which can carry one or more (e.g. 1, 2, 3, 4, 5 or more than 5) substituents. Suitable substituents are chosen e.g. from cycloalkyl, heterocycloalkyl, aryl, hetaryl, halogen, hydroxyl, SH, COOH, carboxylate, $SO_3H$, sulfonate, alkoxy, alkylthio, alkylsulfinyl, alkylsulfonyl, $NE^3E^4$, nitro and cyano, wherein $E^3$ and $E^4$ independently of one another represent hydrogen, alkyl, cycloalkyl, heterocycloalkyl, aryl or hetaryl.

Alkenyl then represents, for example, ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6-dienyl, deca-2,7-dienyl, deca-2,8-dienyl and the like. The statements relating to alkenyl also apply to the alkenyl groups in alkenyloxy, alkenylthio, etc.

In the context of the present invention, the expression "cycloalkyl" includes unsubstituted and also substituted cycloalkyl groups, preferably $C_3$-$C_8$-cycloalkyl groups, such as cyclopropyl, cyclobutyl, cyclopentyl, cyclohexyl, cycloheptyl or cyclooctyl, in particular $C_5$-$C_8$-cycloalkyl. Substituted cycloalkyl groups can contain one or more (e.g. 1, 2, 3, 4, 5 or more than 5) substituents. These are preferably chosen independently of one another from alkyl and the substituents mentioned above for the alkyl groups. In the case of substitution, the cycloalkyl groups preferably carry one or more, for example one, two, three, four or five, $C_1$-$C_6$-alkyl groups.

Examples of preferred cycloalkyl groups are cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl.

The expression "cycloalkenyl" includes unsubstituted and substituted monounsaturated hydrocarbon groups having 3 to 8, preferably 5 to 6 carbon ring members, such as cyclopenten-1-yl, cyclopenten-3-yl, cyclohexen-1-yl, cyclohexen-3-yl, cyclohexen-4-yl and the like. Suitable substituents are those mentioned above for cycloalkyl.

In the context of the present invention, the expression "polycyclyl" includes in the broadest sense compounds which contain at least two rings, independently of how these rings are linked. They can be carbocyclic and/or heterocyclic rings. The rings can be linked via a single or double bond ("polynuclear compounds"), bonded by fusion ("condensed ring systems") or bridged ("bridged ring systems", "cage compounds"). Preferred polycyclic compounds are bridged ring systems and condensed ring systems. Condensed ring systems can be aromatic, hydroaromatic and cyclic compounds linked by fusion (condensed on). Condensed ring systems comprise two, three or more than three rings. Depending on the type of linking, a distinction is made in the case of condensed ring systems between an ortho-fusion, i.e. each ring has in each case one edge or two atoms in common with each adjacent ring, and peri-fusion, in which one carbon atom belongs to more than two rings. Of the condensed ring systems, ortho-condensed ring systems are preferred. In the context of the present invention, the bridged ring systems include those which are not included in the polynuclear ring systems and are not included in the condensed ring systems and in which at least two ring atoms belong to at least two different rings. In the case of bridged ring systems, a distinction is made, according to the number of ring-opening reactions which are formally necessary to arrive at an open-chain compound, between bi-, tri-, tetracyclo compounds etc., which comprise two, three, four etc. rings. In this context, the expression "bicycloalkyl" includes bicyclic hydrocarbon radicals having preferably 5 to 10 C atoms, such as bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl, bicyclo[3.3.0]octyl, bicyclo[4.4.0]decyl and the like.

In the context of the present invention, the expression "aryl" includes mono- or polynuclear aromatic hydrocarbon radicals, which can be unsubstituted or substituted. Aryl preferably represents unsubstituted or substituted phenyl, naphthyl, fluorenyl, anthracenyl, phenanthrenyl, naphthacenyl, chrysenyl, pyrenyl, etc., and particularly preferably phenyl or naphthyl. Substituted aryls can contain one or more (e.g. 1, 2, 3, 4, 5 or more than 5) substituents, depending on the number and size of their ring systems. These are preferably chosen independently of one another from alkyl, alkoxy, cycloalkyl, heterocycloalkyl, aryl, hetaryl, halogen, hydroxyl, SH, alkylthio, alkylsulfinyl, alkylsulfonyl, COOH, carboxylate, $SO_3H$, sulfonate, $NE^5E^6$, nitro and cyano, wherein $E^5$ and $E^6$ independently of one another represent hydrogen, alkyl, cycloalkyl, heterocycloalkyl, aryl or hetaryl. Aryl particularly preferably represents phenyl, which in the case of substitution in general can carry 1, 2, 3, 4 or 5, preferably 1, 2 or 3 substituents.

Aryl, which carries one or more radicals, represents, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl. A further example for substituted aryl, wherein two substituents bound to adjacent carbon atoms of the aryl ring may form together with said carbon atoms a fused ring is indenyl.

In the context of the present invention, the expression "heterocycloalkyl" includes non-aromatic, unsaturated or completely saturated, cycloaliphatic groups having in general 5 to 8 ring atoms, preferably 5 or 6 ring atoms, in which 1, 2 or 3 of the ring carbon atoms are replaced by heteroatoms chosen from oxygen, nitrogen, sulfur and an —$NR^e$— group and which is unsubstituted or substituted by one or more, for example 1, 2, 3, 4, 5 or 6, $C_1$-$C_6$-alkyl groups. $R^e$ preferably represents hydrogen, alkyl, cycloalkyl, hetero-cycloalkyl, aryl or hetaryl. Examples which may be mentioned of such heterocycloaliphatic groups are pyrrolidinyl, piperidinyl, 2,2,6,6-tetramethyl-piperidinyl, imidazolidinyl, pyrazolidinyl, oxazolidinyl, morpholidinyl, thiazolidinyl, isothiazolidinyl, isoxazolidinyl, piperazinyl, tetrahydrothienyl, dihydrothienyl, tetrahydrofuranyl, dihydrofuranyl, tetrahydropyranyl, 1,2-oxazolinyl, 1,3-oxazolinyl and dioxanyl.

In the context of the present invention, the expression "heteroaryl" includes unsubstituted or substituted, heteroaromatic, mono- or polynuclear groups containing, for example, one, two, three or four heteroatoms from the group consisting of O, N, —$NR^e$— or S as ring atoms, preferably the groups pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl, where these heterocycloaromatic groups can carry in general 1, 2 or 3 substituents in the case of substitution. The substituents are preferably chosen from $C_1$-$C_6$-alkyl, $C_1$-$C_6$-alkoxy, hydroxyl, carboxyl, halogen and cyano.

5- to 7-membered nitrogen containing heterocycloalkyl or heteroaryl radicals which optionally contain further heteroatoms represent, for example pyrrolyl, pyrazolyl, imidazolyl, triazolyl, pyrrolidinyl, pyrazolinyl, pyrazolidinyl, imidazolinyl, imidazolidinyl, pyridinyl, pyridazinyl, pyrimidinyl, pyrazinyl, triazinyl, piperidinyl, piperazinyl, oxazolyl, isooxazolyl, thiazolyl, isothiazolyl, indolyl, quinolinyl, isoquinolinyl or quinaldinyl.

Halogen represents fluorine, chlorine, bromine or iodine. In the context of this invention, carboxylate and sulfonate preferably represent a derivative of a carboxylic acid function or of a sulfonic acid function, in particular a metal carboxylate or sulfonate, a carboxylic acid ester or sulfonic acid ester function or a carboxylic acid or sulfonic acid amide function. These include e.g. the esters with $C_1$-$C_4$-alkanols, such as methanol, ethanol, n-propanol, isopropanol, n-butanol, sec-butanol and tert-butanol.

In the context of the present invention, the expression "acyl" represents alkanoyl or aroyl groups having in general 2 to 11, preferably 2 to 8 carbon atoms, for example the acetyl, propanoyl, butanoyl, pentanoyl, hexanoyl, heptanoyl, 2-ethylhexanoyl, 2-propylheptanoyl, benzoyl or naphthoyl group.

The radicals $E^1$ to $E^3$, $E^4$ to $E^6$, $E^7$ to $E^9$ or $E^{10}$ to $E^{12}$ are chosen independently of one another from hydrogen, alkyl, cycloalkyl and aryl. The $NE^1E^2$ groups preferably represent N,N-dimethylamino, N,N-diethylamino, N,N-dipropylamino, N,N-diisopropylamino, N,N-di-n-butylamino, N,N-di-tert-butylamino, N,N-dicyclohexylamino or N,N-diphenylamino.

In the context of the present invention, the expression "the anion equivalent X" represents a monovalent anion or the proportion of a polyvalent anion. The anion $X^-$ serves only as counterion to balance the positively charged groups, and can be selected freely from among monovalent anions and the proportions of polyvalent anions corresponding to a single negative charge. Examples of suitable anions are halide ions $X^-$, e.g. chloride and bromide. Preferred anions are sulfate and sulfonate, e.g. $SO_4^{2-}$, tosylate, trifluoromethanesulfonate and methylsulfonate.

In the compounds of the formula I, the radical R preferably represents hydrogen, alkyl, alkenyl, alkynyl, cycloalkyl, cycloalkenyl, polycyclyl, heterocycloalkyl, aryl or heteroaryl, as defined above.

Preferably, the radical R represents unbranched or branched, unsubstituted or mono- or polysubstituted $C_1$-$C_{18}$-alkyl, wherein the substituents are preferably chosen independently of one another from hydroxyl, halogen, phenyl, cyano, $C_1$-$C_6$-alkoxycarbonyl and $SO_3H$. These include, for example, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl, 1-octadecyl, 2-hydroxyethyl, benzyl, 3-phenylpropyl, 2-cyanoethyl, 2-(methoxycarbonyl)-ethyl, 2-(ethoxycarbonyl)-ethyl, 2-(n-butoxycarbonyl)-ethyl, trifluoromethyl, difluoromethyl, fluoromethyl, pentafluoroethyl, heptafluoropropyl, Heptafluoroisopropyl, nonafluorobutyl, nonafluoroisobutyl, undecylfluoropentyl, undecylfluoroisopentyl, 6-hydroxyhexyl and 3-sulfopropyl.

Preferably, the radical R furthermore represents alkoxyalkyl, hydroxyalkyl, alkoxyalkyloxy or hydroxyalkyloxy, wherein the alkyl groups preferably in each case contain 1 to 14 carbon atoms, in particular 1 to 8 carbon atoms. Preferably, the radical R furthermore represents a polyalkylene oxide having 3 to 100 units and a hydrogen or a $C_1$-$C_8$-alkyl as the end group, such as, for example, $R^A O$—$(CHR^B$—$CH_2$—$O)_m$—$CHR^B$—$CH_2$— or $R^A O$—$(CH_2CH_2CH_2CH_2O)_m$—$CH_2CH_2CH_2CH_2O$, where $R^A$ and $R^B$ are preferably hydrogen, methyl or ethyl and m is preferably 0 to 3, in particular 3-oxabutyl, 3-oxapentyl, 3,6-dioxaheptyl, 3,6-dioxaoctyl, 3,6,9-trioxadecyl, 3,6,9-trioxaundecyl, 3,6,9,12-tetraoxamidecyl and 3,6,9,12-tetraoxatetradecyl.

Preferably, the radical R furthermore represents vinyl or allyl.

Particularly preferably, the radical R represents hydrogen and unbranched and unsubstituted $C_1$-$C_{18}$-alkyl, in particular methyl, ethyl, 1-propyl, 1-butyl, 1-pentyl, 1-hexyl, 1-heptyl, 1-octyl, 1-decyl, 1-dodecyl, 1-tetradecyl, 1-hexadecyl or 1-octadecyl, as well as allyl.

Specifically, the radical R represents hydrogen, methyl, ethyl, 1-butyl and 1-octyl.

Preferably, in the compounds of the formula I, the cations are chosen from cations of the formulae I.1 or I.2

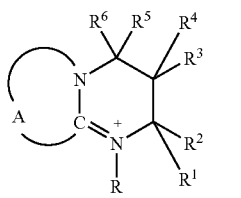
(I.1)

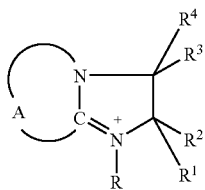
(I.2)

wherein
R and A have the abovementioned meanings, and
$R^1$, $R^2$, $R^3$, $R^4$, $R^5$ and $R^6$ independently of one another represent hydrogen, alkyl, alkenyl, cycloalkyl, cycloalkenyl, polycyclyl, heterocycloalkyl, aryl, hetaryl, hydroxyl, SH, polyalkylene oxide, polyalkyleneimine, alkoxy, alkylthio, alkylsulfinyl, alkylsulfonyl, halogen, $SO_3H$, sulfonate, $NE^1E^2$, nitro, alkoxycarbonyl, COOH, carboxylate, formyl, acyl or cyano, wherein $E^1$ and $E^2$ denote in each case identical or different radicals chosen from hydrogen, alkyl, cycloalkyl and aryl,
wherein the radicals $R^1$, $R^2$, $R^3$, $R^4$, $R^5$ and $R^6$ which represent alkyl radicals can contain 1, 2, 3, 4 or 5 substituents chosen from cycloalkyl, heterocycloalkyl, aryl, hetaryl, cycloalkoxy, cycloalkylthio, heterocycloalkoxy, heterocycloalkylthio, aryloxy, arylthio, hetaryloxy, hetarylthio, hydroxyl, SH, COOH, carboxylate, $SO_3H$, sulfonate, $NE^4E^5$, $(NE^4E^5E^6)^+X^-$, halogen, nitro, formyl, acyl and cyano, wherein $E^4$, $E^5$ and $E^6$ denote in each case identical or different radicals chosen from hydrogen, alkyl, cycloalkyl and aryl and $X^-$ represents an anion equivalent,
and wherein the radicals $R^1$, $R^2$, $R^3$, $R^4$, $R^5$ and $R^6$ which represent cycloalkyl, cycloalkenyl, polycyclyl, heterocycloalkyl, aryl and hetaryl radicals can contain 1, 2, 3, 4 or 5 substituents which are chosen from alkyl and the substituents mentioned above for the alkyl radicals $R^1$ to $R^6$, or $R^1$ and $R^2$ and/or, if present, $R^4$ and $R^6$, together with the ring carbons to which they are bonded, represent a 5- to 8-membered saturated, unsaturated or aromatic carbo- or heterocyclic radical, which is optionally additionally fused with one, two or three cycloalkyl, heterocycloalkyl, aryl or hetaryl, wherein the carbo- or heterocyclic radical and, if present, the fused-on groups independently of one another can each carry one, two, three or four substituents which are chosen from alkyl, cycloalkyl, heterocycloalkyl, aryl, hetaryl, hydroxyl, SH, halogen, COOH, carboxylate, $SO_3H$, sulfonate, $NE^7E^8$, $(NE^7E^8E^9)^+X^-$, nitro, alkoxycarbonyl, formyl, acyl and cyano, wherein $E^7$, $E^8$ and $E^9$ denote in each case identical or different radicals chosen from hydrogen, alkyl, cycloalkyl and aryl and $X^-$ represents an anion equivalent,
wherein in the compounds of the formula I.1, $R^1$ and $R^3$ or $R^3$ and $R^5$ also together can represent the bond portion of a double bond between the ring atoms which carry these radicals.

Preferably, in the compounds of the formula I.1 and I.2, the group A represents a 4- to 8-membered, saturated or unsaturated or aromatic ring, which is optionally substituted and/or which can optionally contain further heteroatoms or heteroatom-containing groups and/or which can include further fused-on saturated, unsaturated or aromatic carbocyclic rings or heterocyclic rings.

Particularly preferably, A, together with the C—N group to which it is bonded, represents a 5- to 8-membered ring, which is optionally additionally fused with one, two or three cycloalkyl, cycloalkenyl, heterocycloalkyl, aryl or hetaryl, wherein the heterocyclic radical and, if present, the fused-on groups independently of one another can each carry one, two, three or four substituents which are chosen from alkyl, cycloalkyl, cycloalkenyl, heterocycloalkyl, aryl, hetaryl, hydroxyl, SH, polyalkylene oxide, polyalkyleneimine, alkoxy, halogen, COOH, carboxylate, $SO_3H$, sulfonate, $NE^{10}E^{11}$, $(NE^{10}E^{11}E^{12})^+X^-$, nitro, alkoxycarbonyl, formyl, acyl and cyano, wherein $E^{10}$, $E^{11}$ and $E^{12}$ denote in each case identical or different radicals chosen from hydrogen, alkyl, cycloalkyl and aryl and $X^-$ represents an anion equivalent.

Particularly preferably, A represents an unsubstituted, linear $C_2$-$C_6$-alkylene bridge, in particular an unsubstituted $C_3$-$C_5$-alkylene bridge.

Preferably, in the compounds of the formula I, the cations are chosen from cations of 1,5-diazabicyclo[4.3.0]non-5-ene (DBN) and 1,8-diazabicyclo[5.4.0]undec-7-ene (DBU).

Preferably, in the cations of the formulae I.1 or I.2 the radical R is selected from hydrogen and $C_1$-$C_{12}$ alkyl. More preferably, R is selected from hydrogen and $C_1$-$C_{10}$ alkyl.

Among the cations of the formula I.1, a 1,8-diazabicyclo [5.4.0]undec-7-enium cation

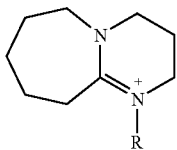

wherein R is hydrogen or $C_1$-$C_{12}$ alkyl, in particular $C_1$-$C_{10}$ alkyl, specially methyl, ethyl, butyl, hexyl or octyl, in particular hydrogen, methyl, butyl or octyl is most preferred.

A further object of the invention is a compound of the formula I.2a and their salts I.2b

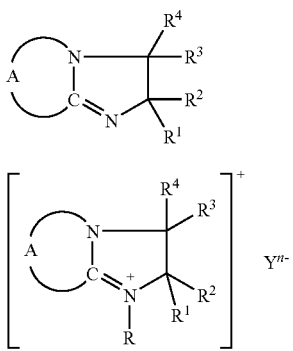

wherein
A together with the C—N group to which it is bonded, forms a 4- to 8-membered, saturated or unsaturated or aromatic ring, which is optionally substituted and/or which can optionally contain further heteroatoms or heteroatom-containing groups and/or which can include further fused-on saturated, unsaturated or aromatic carbocyclic rings or heterocyclic rings,
R represents hydrogen or an organyl radical,
$R^1$, $R^2$, $R^3$ and $R^4$ independently of one another represent hydrogen, alkyl, alkenyl, cycloalkyl, cycloalkenyl, polycyclyl, heterocycloalkyl, aryl, hetaryl, hydroxyl, SH, polyalkylene oxide, polyalkyleneimine, alkoxy, alkylthio, alkylsulfinyl, alkylsulfonyl, halogen, $SO_3H$, sulfonate, $NE^1E^2$, nitro, alkoxycarbonyl, COOH, carboxylate, formyl, acyl or cyano, wherein $E^1$ and $E^2$ denote in each case identical or different radicals chosen from hydrogen, alkyl, cycloalkyl and aryl,
wherein the radicals $R^1$, $R^2$, $R^3$ and $R^4$ which represent alkyl radicals can contain 1, 2, 3, 4 or 5 substituents chosen from cycloalkyl, heterocycloalkyl, aryl, hetaryl, cycloalkoxy, cycloalkylthio, heterocycloalkoxy, heterocycloalkylthio, aryloxy, arylthio, hetaryloxy, hetarylthio, hydroxyl, SH, COOH, carboxylate, $SO_3H$, sulfonate, $NE^4E^5$, $(NE^4E^5E^6)^+X^-$, halogen, nitro, formyl, acyl and cyano, wherein $E^4$, $E^5$ and $E^6$ denote in each case identical or different radicals chosen from hydrogen, alkyl, cycloalkyl and aryl and $X^-$ represents an anion equivalent, and wherein the radicals $R^1$, $R^2$, $R^3$ and $R^4$ which represent cycloalkyl, cycloalkenyl, polycyclyl, heterocycloalkyl, aryl and hetaryl radicals can contain 1, 2, 3, 4 or 5 substituents which are chosen from alkyl and the substituents mentioned above for the alkyl radicals $R^1$ to $R^6$, or
$R^1$ and $R^3$, together with the ring carbons to which they are bonded, represent a 5- to 8-membered saturated, unsaturated or aromatic carbo- or heterocyclic radical, which is optionally additionally fused with one, two or three cycloalkyl, heterocycloalkyl, aryl or hetaryl, wherein the carbo- or heterocyclic radical and, if present, the fused-on groups independently of one another can each carry one, two, three or four substituents which are chosen from alkyl, cycloalkyl, heterocycloalkyl, aryl, hetaryl, hydroxyl, SH, halogen, COOH, carboxylate, $SO_3H$, sulfonate, $NE^7E^8$, $(NE^7E^8E^9)^+X^-$, nitro, alkoxycarbonyl, formyl, acyl and cyano, wherein $E^7$, $E^8$ and $E^9$ denote in each case identical or different radicals chosen from hydrogen, alkyl, cycloalkyl and aryl and $X^-$ represents an anion equivalent,
wherein in the compounds of the formula I.1, $R^1$ and $R^3$ or $R^3$ and $R^5$ also together can represent the bond portion of a double bond between the ring atoms which carry these radicals,
$Y^{n-}$ represents a mono-, di-, tri- or tetravalent anion, and
n represents one, two, three or four.

Suitable and preferred embodiments of A, R, $R^1$, $R^2$, $R^3$ and $R^4$ are those mentioned before.

All anions can in principle be employed as anions. The anion $Y^{n-}$ of the ionic liquids employed according to the invention is chosen, for example, from
halides, pseudohalides and halogen-containing compounds of the formulae:
$F^-$, $Cl^-$, $Br^-$, $I^-$, $PF_6^-$, $CF_3SO_3^-$, $(CF_3SO_3)_2N^-$, $CF_3CO_2^-$, $CCl_3CO_2^-$, $CN^-$, $SCN^-$, $OCN^-$;
sulfates, sulfites and sulfonates of the general formulae:
$SO_4^{2-}$, $HSO_4^-$, $SO_3^{2-}$, $HSO_3^-$, $R^aOSO_3^-$, $R^aSO_3^-$;
phosphates of the general formulae:
$PO_4^{3-}$, $HPO_4^{2-}$, $H_2PO_4^-$, $R^aPO_4^{2-}$, $HR^aPO_4^-$, $R^aR^bPO_4^-$;
phosphonates and phosphinates of the general formulae:
$R^aHPO_3^-$, $R^aR^bPO_2^-$, $R^aR^bPO_3^-$;
phosphites of the general formulae:
$PO_3^{3-}$, $HPO_3^{2-}$, $H_2PO_3^-$, $R^aPO_3^{2-}$, $R^aHPO_3^-$, $R^aR^bPO_3^-$;
phosphonites and phosphinites of the general formulae:
$R^aR^bPO_2^-$, $R^aHPO_2^-$, $R^aR^bPO^-$, $R^aHPO^-$;
carboxylic acid anions of the general formula:
$R^aCOO^-$;
hydroxycarboxylic acids anions and sugar acid anions;
saccharinates (salts of o-benzoic acid sulfimide);
borates of the general formulae:
$BO_3^{3-}$, $HBO_3^{2-}$, $H_2BO_3^-$, $R^aR^bBO_3^-$, $R^aHBO_3^-$, $R^aBO_3^{2-}$, $B(OR^a)(OR^b)(OR^c)(OR^d)^-$, $B(HSO_4)^-$, $B(R^aSO_4)^-$;
boronates of the general formulae:
$R^aBO_2^{2-}$, $R^aR^bBO^-$;
carbonates and carbonic acid esters of the general formulae:
$HCO_3^-$, $CO_3^{2-}$, $R^aCO_3^-$;
silicates and silicic acid esters of the general formulae:
$SiO_4^{4-}$, $HSiO_4^{3-}$, $H_2SiO_4^{2-}$, $H_3SiO_4^-$, $R^aSiO_4^{3-}$, $R^aR^b SiO_4^{2-}$, $R^aR^bR^cSiO_4^-$, $HR^aSiO_4^{2-}$, $H_2R^aSiO_4^-$, $HR^aR^b SiO_4^-$;
alkyl- and arylsilanolates of the general formulae:
$R^aSiO_3^{3-}$, $R^aR^bSiO_2^{2-}$, $R^aR^bR^cSiO_3^-$, $R^aR^bR^cSiO_3^-$, $R^aR^bR^cSiO_2^-$, $R^aR^bSiO_3^{2-}$;
carboxylic acid imides, bis(sulfonyl)imides and sulfonylimides of the general formulae:

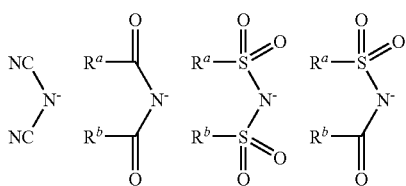

methides of the general formula:

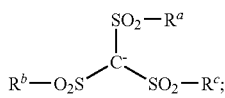

alkoxides and aryloxides of the general formula:
$R^aO^-$;
sulfides, hydrogen sulfides, polysulfides, hydrogen polysulfides and thiolates of the general formulae:
$S^{2-}$, $HS^-$, $[S_v]^{2-}$, $[HS_v]^-$, $[R^aS]^-$,
wherein v is a whole positive number of from 2 to 10.

Preferably, the radicals $R^a$, $R^b$, $R^c$ and $R^d$ are chosen independently of one another from hydrogen, alkyl, cycloalkyl, heterocycloalkyl, aryl, hetaryl and polycyclyl. Particularly preferably, the radicals $R^a$, $R^b$, $R^c$ and $R^d$ are chosen independently of one another from optionally substituted $C_1$-$C_{30}$-alkyl, $C_2$-$C_{18}$-alkyl radicals in which the carbon chains are interrupted by one or more non-adjacent groups, optionally substituted $C_6$-$C_{14}$-aryl, optionally substituted $C_5$-$C_{12}$-cycloalkyl, optionally substituted heterocycloalkyl having 5 or 6 ring atoms, optionally substituted hetaryl having 5 or 6 ring atoms and optionally substituted polycyclic radicals having 6 to 24 ring atoms. In respect of suitable and preferred embodiments, reference is made to the definitions given above for these radicals in their full scope.

Preferred anions are chosen from halides, pseudohalides, halogen-containing compounds, carboxylic acid anions, hydroxycarboxylic acid anions, sugar acid anions, sulfates, sulfites, sulfonates and phosphates.

Particularly preferred anions are chloride, bromide, iodide, $SCN^-$, $OCN^-$, $CN^-$, formate, acetate, propionate, butyrate, lactate, saccharinate, methyl-sulfate, ethyl-sulfate, methanesulfonate, tosylate, trifluoroacetate, dimethyl-phosphate, diethyl-phosphate, di-(2-ethylhexyl)-phosphate and hydrogen sulfate.

Among the ionic liquid of the general formula I, a 1,8-diazabicyclo[5.4.0]undec-7-enium cation

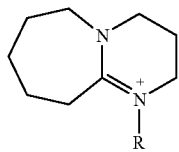

wherein R is hydrogen or $C_1$-$C_{12}$ alkyl, in particular $C_1$-$C_{10}$ alkyl, specially methyl, ethyl, butyl, hexyl or octyl, in particular hydrogen, methyl, butyl or octyl is most preferred and chloride, hydrogen sulfate, dimethyl phosphate, $SCN^-$, formate, acetate, trifluoroacetate, lactate, saccharinate, tosylate, methanesulfonate and trifluoromethane sulfamate are the most preferred anions.

Preferably, the liquid compositions according to the invention comprise at least one completely solubilized polymer in an amount of at least 1 wt. %, based on the total weight of the composition. More preferably, more than 3 wt. %, particularly preferably more than 5 wt. % and especially preferably at least 7 wt. %, based on the total weight of the composition, is completely solubilized.

Preferably, the liquid compositions according to the invention comprise at least one completely solubilized polymer in an amount of up to 30 wt. %, particularly preferably up to 35 wt. %, based on the total weight of the composition.

A preferred embodiment of the present invention relates to a liquid composition which comprises a halogen-containing polymer as the polymer. Halogen-containing polymers include polychloroprene, chlorinated and fluorinated rubbers, chlorinated and brominated copolymer of isobutylene/isoprene (halogen rubber), chlorinated and sulfochlorinated polyethylene, copolymers of ethylene and chlorinated ethylene, epichlorohydrin homo- and copolymers, in particular polymers of halogen-containing vinyl compounds, e.g. polyvinyl chloride (PVC), polyvinylidene chloride (PVDC), polyvinyl fluoride, polyvinylidene fluoride and copolymers thereof, such as vinyl chloride/vinylidene chloride, vinyl chloride/vinyl acetate or vinylidene chloride/vinyl acetate copolymers. Polyvinyl chloride is employed with a varying content of plasticizers, with a content of plasticizers of 0-12% as rigid PVC, of more than 12% as plasticized PVC or with a very high content of plasticizers as PVC paste. Conventional plasticizers are e.g. phthalates, epoxides and adipic acid esters.

Polyvinyl chloride is prepared by free-radical polymerization of vinyl chloride in bulk, suspension, microsuspension and emulsion polymerization. PVC is employed in diverse uses, for example as foamed imitation leather, insulating wallpapers, domestic articles, shoe soles, furniture profiles, floor coverings or pipes.

Polyvinylidene chloride is prepared by free-radical polymerization of vinylidene chloride. Vinylidene chloride can also be copolymerized with (meth)acrylates, vinyl chloride or acrylonitrile. Polyvinylidene chloride and the vinylidene copolymers are processed, for example, to films, and also to profiles, pipes and fibers.

A further preferred embodiment of the present invention relates to liquid compositions, wherein the polymer is chosen from homopolymers and copolymers of cyclic ethers, such as polyalkylene glycols, e.g. polyethylene oxide, polypropylene oxide or copolymers thereof with bisglycidyl ethers. Polyalkylene glycols are formed by polyaddition of an cyclic ether, such as, for example, ethylene oxide, propylene oxide or tetrahydrofuran, with an OH compound as the starter molecule, such as water. Starter molecules for the polyaddition can also be di- or polyhydric alcohols. Low molecular weight polyalkylene glycols are employed as synthetic lubricants. Polyalkylene glycols are furthermore employed as solubilizing agents for surfactant combinations, as binders in soaps, as constituents in inks and stamp inks, and as plasticizers and release agents.

A further preferred embodiment of the present invention relates to liquid compositions, wherein the polymer is chosen from polyacetals, copolymers of polyacetals with cyclic ethers and polyacetals which are modified with thermoplastic polyurethanes, acrylates or methyl acrylate/butadiene/styrene copolymers. Polyacetals are formed by polymerization of aldehydes or of cyclic acetals. An industrially important polyacetal is polyoxymethylene (POM), which is obtainable by cationic or anionic polymerization of formaldehyde or trioxane. Modified POM is obtained, for example, by copolymerization with cyclic ethers, such as ethylene oxide or 1,3-dioxolane. Combination of POM with thermoplastic polyurethane elastomers gives POM-based polymer blends. Non-reinforced POM is distinguished by a very high rigidity, strength and toughness. POM is preferably used for domestic appliance and apparatus construction, vehicle construction, machine construction and sanitary and installation engineering.

A further preferred embodiment of the present invention relates to liquid compositions, wherein the polymer is chosen from polyaryl ethers, polyaryl sulfides and mixtures of polyaryl ethers with styrene polymers and polyamides. An example of polyaryl ethers are polyphenylene oxides, the main chain of which is built up from phenylene units which are linked via oxygen atoms and are optionally substituted by alkyl groups. An industrially important polyphenylene oxide is poly-2,6-dimethylphenyl ether. An example of polyaryl sulfides are polyphenylene sulfides, which are obtainable by polycondensation of 1,4-dichlorobenzene with sodium sulfide. They are distinguished by a high strength, rigidity and hardness. They are suitable as a substitute for metals in construction of pump housings and in other elements of machine and apparatus construction. Further fields of use for polyphenylene sulfides are electrical engineering and electronics.

A further preferred embodiment of the present invention relates to liquid compositions, wherein the polymer is chosen from polyurethanes. Suitable polyisocyanate polyaddition products (polyurethanes) are, for example, cellular polyurethanes, e.g. rigid or flexible polyurethane foams, compact polyurethanes, thermoplastic polyurethanes (TPU), thermosetting or elastic polyurethanes or polyisocyanurates. These are generally known and their preparation is described in many instances. It is conventionally carried out by reaction of di- and more highly functional isocyanates or of corresponding isocyanate analogs with compounds which are reactive towards isocyanates. The preparation is carried out by conventional processes, for example in the one-shot process or by the prepolymer process, e.g. in molds, in a reaction extruder or also a belt installation. A specific preparation process is the reaction injection molding (RIM) process, which is preferably used for the preparation of polyurethanes having a foamed or compact core and a predominantly compact, non-porous surface.

Polyurethanes are in general built up from at least one polyisocyanate and at least one compound having at least two groups per molecule which are reactive towards isocyanate groups. Suitable polyisocyanates preferably have 2 to 5 NCO groups. The groups which are reactive towards isocyanate groups are preferably chosen from hydroxyl, mercapto and primary and secondary amino groups. These include, preferably, di- or more highly hydric polyols.

Suitable polyisocyanates are aliphatic, cycloaliphatic, araliphatic and aromatic isocyanates. Suitable aromatic diisocyanates are, for example, 2,2'-, 2,4'- and/or 4,4'-diphenylmethane diisocyanate (MDI), 1,5-naphthylene diisocyanate (NDI), 2,4- and/or 2,6-toluoylene diisocyanate (TDI), diphenylmethane diisocyanate, 3,3'-dimethyl-diphenyl diisocyanate, 1,2-diphenylethane diisocyanate and/or phenylene diisocyanate. Aliphatic and cycloaliphatic diisocyanates include, for example, tri-, tetra-, penta-, hexa-, hepta- and/or octamethylene diisocyanate, 2-methyl-pentamethylene-1,5-diisocyanate, 2-ethylbutylene-1,4-diisocyanate, 1-isocyanato-3,3,5-trimethyl-5-isocyanatomethyl-cyclohexane (isophorone diisocyanate, IPDI), 1,4- and/or 1,3-bis(isocyanatomethyl) cyclohexane (HXDI), cyclohexane-1,4-diisocyanate, 1-methyl-2,4- and/or 2,6-cyclohexane diisocyanato and/or 4,4'-, 2,4'- and/or 2,2'-dicyclohexylmethane diisocyanate. The preferred diisocyanates include hexamethylene diisocyanate (HMDI) and isophorone diisocyanate. Examples of more highly functional isocyanates are triisocyanates, e.g. triphenylmethane-4,4',4"-triisocyanate, and furthermore the cyanurates of the abovementioned diisocyanates, as well as the oligomers obtainable by partial reaction of diisocyanates with water, e.g. the biurets of the abovementioned diisocyanates, and furthermore oligomers which are obtainable by controlled reaction of semi-blocked diisocyanates with polyols which contain on average more than 2 and preferably 3 or more hydroxyl groups.

In this context, polyol components which are employed for polyurethane rigid foams, which can optionally contain isocyanurate structures, are highly functional polyols, in particular polyether polyols based on highly functional alcohols, sugar alcohols and/or saccharides as starter molecules. For flexible polyisocyanate polyaddition products, e.g. polyurethane flexible foams or RIM materials, 2- and/or 3-functional polyether polyols based on glycerol and/or trimethylolpropane and/or glycols as starter molecules are preferred as polyols and 2- and/or 3-functional polyester polyols based on glycerol and/or trimethylolpropane and/or glycols as alcohols to be esterified are preferred as polyols. Thermoplastic polyurethanes are conventionally based on predominantly difunctional polyester polyalcohols and/or polyether polyalcohols, which preferably have an average functionality of from 1.8 to 2.5, particularly preferably 1.9 to 2.1.

In this context, the polyether polyols are prepared by a known technology. Suitable alkylene oxides for the preparation of the polyols are, for example, 1,3-propylene oxide, 1,2- or 2,3-butylene oxide, styrene oxide and, preferably, ethylene oxide and 1,2-propylene oxide. The alkylene oxides can be used individually, alternately in succession or as mixtures. Preferably, alkylene oxides which lead to primary hydroxyl groups in the polyol are used. Particularly preferably, polyols which are employed are those which have been alkoxylated with ethylene oxide to conclude the alkoxylation and therefore contain primary hydroxyl groups. Further suitable polyetherols are polytetrahydrofurans and polyoxymethylenes. The polyether polyols have a functionality of preferably from 2 to 6, and in particular 2 to 4, and molecular weights of from 200 to 10,000, preferably 200 to 8,000.

Suitable polyester polyols can be prepared, for example, from organic dicarboxylic acids having 2 to 12 carbon atoms, preferably aliphatic dicarboxylic acids having 4 to 6 carbon atoms, and polyhydric alcohols, preferably diols, having 2 to 12 carbon atoms, preferably 2 to 6 carbon atoms. The polyester polyols preferably have a functionality of from 2 to 4, in particular 2 to 3, and a molecular weight of from 480 to 3,000, preferably 600 to 2,000 and in particular 600 to 1,500.

The polyol component can furthermore also include diols or more highly hydric alcohols. Suitable diols are glycols having preferably 2 to 25 carbon atoms. These include 1,2-ethanediol, 1,2-propanediol, 1,3-propanediol, 1,4-butanediol, 1,5-pentanediol, 1,6-hexanediol, 1,10-decanediol, diethylene glycol, 2,2,4-trimethylpentane-1,5-diol, 2,2-dimethylpropane-1,3-diol, 1,4-dimethylolcyclohexane, 1,6-dimethylolcyclohexane, 2,2-bis(4-hydroxyphenyl)-propane (bisphenol A), 2,2-bis(4-hydroxyphenyl)butane (bisphenol B) or 1,1-bis(4-hydroxyphenyl)-3,3,5-trimethylcyclohexane (bisphenol C). Suitable more highly hydric alcohols are e.g. trihydric (triols), tetrahydric (tetrols) and/or pentahydric alcohols (pentols). As a rule, they contain 3 to 25, preferably 3 to 18 carbon atoms. These include glycerol, trimethylolethane, trimethylolpropane, erythritol, pentaerythritol, sorbitol and alkoxylates thereof.

However, the addition of chain-lengthening agents, crosslinking agents, terminators or optionally also mixtures thereof may prove advantageous for modification of the mechanical properties, e.g. the hardness. The chain-lengthening and/or crosslinking agents have, for example, a molecular weight of from 40 to 300. Possible compounds are, for example, aliphatic, cycloaliphatic and/or araliphatic diols having 2 to 14, preferably 2 to 10 carbon atoms, such as e.g. ethylene glycol, 1,3-propanediol, 1,2-propanediol, 1,10-decanediol, 1,2-, 1,3-, 1,4-dihydroxycyclohexane, diethylene glycol, dipropylene glycol and, preferably, ethylene glycol, 1,4-butanediol, 1,6-hexanediol and bis-(2-hydroxyethyl)-hydroquinone, triols, such as 1,2,4-, 1,3,5-trihydroxycyclohexane, glycerol, trimethylolpropane and triethanolamine, and low molecular weight polyalkylene oxides containing hydroxyl groups and based on ethylene oxide and/or 1,2-propylene oxide and the abovementioned diols and/or triols as starter molecules. Suitable terminators include, for example, monofunctional alcohols or secondary amines.

Polyurethanes are mostly processed to foams.

A further preferred embodiment of the present invention relates to liquid compositions, wherein the polymer is chosen from polyureas, polyimides, polyamide-imides, polyether-imides, polyester-imides, polyhydantoins and polybenzimidazoles. As is known, polyureas are formed by polyaddition of diamines and diisocyanates.

Polyimides, the essential structural element of which is the imide group in the main chain, are formed by reaction of aromatic tetracarboxylic acid dianhydrides with aliphatic or aromatic diamines. Polyimides are employed, inter alia, as adhesives in composite materials, and moreover for coatings, thin films, for example as insulating material in microelectronics, for high modulus fibers, for semipermeable membranes and as liquid crystal polymers.

A further preferred embodiment of the present invention relates to liquid compositions, wherein the polymer is chosen from polyesters. Suitable polyesters and copolyesters are described in EP-A-0678376, EP-A-0 595 413 and U.S. Pat. No. 6,096,854, to which reference is herewith made. As is known, polyesters are condensation products of one or more polyols and one or more polycarboxylic acids. In linear polyesters, the polyol is a diol and the polycarboxylic acid is a dicarboxylic acid. The diol component can be chosen from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol and 1,3-cyclohexanedimethanol. Diols in which the alkylene chain is interrupted once or several times by non-adjacent oxygen atoms are furthermore possible. These include diethylene glycol, triethylene glycol, dipropylene glycol, tripropylene glycol and the like. As a rule, the diol contains 2 to 18 carbon atoms, preferably 2 to 8 carbon atoms. Cycloaliphatic diols can be employed in the form of their cis or trans isomers or as an isomer mixture. The acid component can be an aliphatic, alicyclic or aromatic dicarboxylic acid. The acid component of linear polyesters is as a rule chosen from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalenedicarboxylic acid and mixtures thereof. The functional derivatives of the acid component, such as esters, for example methyl ester, anhydrides or halides, preferably chlorides, can of course also be employed. Preferred polyesters are polyalkylene terephthalates, and polyalkylene naphthalates, which are obtainable by condensation of terephthalic acid or, respectively, naphthalenedicarboxylic acid with an aliphatic diol.

Polyethylene terephthalates PET and polybutylene terephthalates PBT are widely employed for production of fibers, and moreover have a high resistance as thermoplastic materials for industrial parts, such as bearings, toothed wheels, cam disks, pulleys, switch housings, plugs, handles and control buttons. PET is used to a high degree as a material for drinks bottles.

A further preferred embodiment of the present invention relates to liquid compositions, wherein the polymer is chosen from polycarbonates, polyester carbonates and mixtures thereof. Polycarbonates are formed e.g. by condensation of phosgene or carbonic acid esters, such as diphenyl carbonate or dimethyl carbonate, with dihydroxy compounds. Suitable dihydroxy compounds are aliphatic or aromatic dihydroxy compounds. Aromatic dihydroxy compounds which may be mentioned are, for example, bisphenols, such as 2,2-bis-(4-hydroxyphenyl)-propane (bisphenol A), tetraalkylbisphenol-A, 4,4-(meta-phenylenediisopropyl)diphenol (bisphenol M), 4,4-(para-phenylenediisopropyl)diphenol, 1,1-bis-(4-hydroxyphenyl)-3,3,5-trimethyl-cyclohexane (BP-TMC), 2,2-bis-(4-hydroxyphenyl)-2-phenylethane, 1,1-bis-(4-hydroxyphenyl)-cyclohexane (bisphenol Z) and optionally mixtures thereof. The polycarbonates can be branched by using small amounts of branching agents. Suitable branching agents include phloroglucinol, 4,6-dimethyl-2,4,6-tri-(4-hydroxyphenyl)-hept-2-ene, 4,6-dimethyl-2,4,6-tri(4-hydroxyphenyl)-heptane; 1,3,5-tri-(4-hydroxyphenyl)-benzene; 1,1,1-tri (4-hydroxyphenyl)-heptane; 1,3,5-tri-(4-hydroxyphenyl)-benzene; 1,1,1-tri-(4-hydroxyphenyl)-ethane; tri-(4-hydroxyphenyl)-phenylmethane, 2,2-bis-[4,4-bis-(4-hydroxyphenyl)-cyclohexyl]-propane; 2,4-bis-(4-hydroxyphenyl-isopropyl)-phenol; 2,6-bis(2-hydroxy-5'-methyl-benzyl)-4-methylphenol; 2-(4-hydroxyphenyl)-2-(2,4-dihydroxyphenyl)-propane; hexa-(4-(4-hydroxyphenyl-isopropyl)-phenyl)-orthoterephthalic acid ester; tetra-(4-hydroxyphenyl)-methane; tetra-(4-(4-hydroxyphenyl-isopropyl)-phenoxy)-methane; α,α',α"-tris-(4-hydroxyphenyl)-1,3,5-triisopropylbenzene; 2,4-dihydroxybenzoic acid; trimesic acid; cyanuric chloride; 3,3-bis-(3-methyl-4-hydroxyphenyl)-2-oxo-2,3-dihydroindole, 1,4-bis-(4',4"-dihydroxytriphenyl)-methyl)-benzene and, in particular 1,1,1-tri-(4-hydroxyphenyl)-ethane and bis-(3-methyl-4-hydroxyphenyl)-2-oxo-2,3-dihydroindole.

Phenols, such as phenol, alkylphenols, such as cresol and 4-tert-butylphenol, chlorophenol, bromophenol, cumylphenol or mixtures thereof are suitable, for example, for chain termination. The content of chain terminators is as a rule 1 to 20 mol % per mol of dihydroxy compound.

A further preferred embodiment of the present invention relates to liquid compositions, wherein the polymer is chosen from polysulfones, polyether sulfones, polyether ketones and mixtures thereof. Polyether ketones are employed, for example, in the electrical industry and in vehicle construction.

A further preferred embodiment of the present invention relates to liquid compositions, wherein the polymer is chosen from synthetic resins. Synthetic resins include crosslinked polymers which are derived from aldehydes on the one hand and phenols, and ureas on the other hand, such as phenol-formaldehyde resins, and urea-formaldehyde resins. Synthetic resins likewise include drying and non-drying alkyd resins and unsaturated polyester resins derived from copolyesters of saturated and unsaturated dicarboxylic acids with polyhydric alcohols and vinyl compounds as crosslinking agents and also halogen-containing modifications thereof of low flammability. Synthetic resins furthermore include crosslinkable acrylic resins which are derived from substituted acrylates, such as epoxyacrylates, urethane acrylates or polyester acrylates. Synthetic resins furthermore include alkyd resins, polyester resins and acrylate resins, crosslinked with urea resins, isocyanates, isocyanurates, polyisocyanates or epoxy resins and crosslinked epoxy resins which are derived from aliphatic, cycloaliphatic, heterocyclic or aromatic glycidyl compounds. As is known, epoxy resins are formed by a ring-opening crosslinking reaction of polyfunctional epoxides. Examples of epoxy resins include diglycidyl ethers of bisphenol A or bisphenol F. They can be crosslinked with acid anhydrides or amines, with or without an accelerator.

A further preferred embodiment of the present invention relates to a liquid composition, wherein the polymer is chosen from naturally occurring and synthetic organic materials which are prepared from pure monomeric compounds or mixtures of such compounds, e.g. mineral oils, animal and plant fats, oils and waxes, or oils, fats and waxes which are based on synthetic esters, such as phthalates, adipates, phosphates or trimellitates, and also mixtures of synthetic esters with mineral oils in any desired weight ratios, in general those which are used as spinning agents, as well as aqueous emulsions of such materials.

A further preferred embodiment of the present invention relates to a liquid composition, wherein the polymer is chosen from aqueous emulsions of natural or synthetic rubber. Aqueous emulsions of natural or synthetic rubber include natural latex or latices of carboxylated styrene/butadiene copolymers.

A further preferred embodiment of the invention relates to a liquid composition, wherein the polymer is chosen from polymers which are derived from unsaturated alcohols and amines or from acyl derivatives or acetals thereof, such as polyvinyl acetate (PVAC) and polyvinyl alcohol (PVAL). Polyvinyl acetals are formed in the reaction of polyvinyl alcohol with an aldehyde, for example polyvinyl formals (PVFM) in the reaction with formaldehyde or polyvinyl butyrals (PVB) with butyraldehyde. Because of their low glass transition temperature, polyvinyl compounds are not thermoplastic materials but polymer resins. They are employed as coating compositions, for example for carpet backing coatings, cheese coatings, paper coating compositions, lacquer and pigment binders, lacquer raw material, sizes, adhesives, protective colloids, chewing gum base, concrete admixture, films for production of laminated glass for windscreens of motor vehicles and for many other purposes.

A further preferred embodiment of the invention relates to a liquid composition, wherein the polymer is chosen from polyamides (abbreviated to PA) or copolyamides which contain amide groups as the essential structural element in the polymer main chain. Polyamides can be prepared, for example, by polycondensation from diamines and dicarboxylic acids or derivatives thereof. Suitable diamines are, for example, alkyldiamines, such as $C_2$-$C_{20}$-alkyldiamines, e.g. hexamethylenediamine, or aromatic diamines, such as $C_6$- to $C_{20}$-aromatic diamines, e.g. m- or p-phenylenediamine or m-xylenediamine. Suitable dicarboxylic acids include aliphatic dicarboxylic acids or derivatives thereof, for example chlorides, such as $C_2$- to $C_{20}$-aliphatic dicarboxylic acid, e.g. sebacic acid, decanedicarboxylic acid or adipic acid, or aromatic dicarboxylic acids, for example, $C_6$- to $C_{20}$-aromatic dicarboxylic acids or derivatives thereof, for example chlorides, such as 2,6-naphthalenedicarboxylic acid, isophthalic acid or terephthalic acid. Examples of such polyamides are poly-2,4,4-trimethylhexamethyleneterephthalamide or poly-m-phenyleneisophthalamide, PA 66 (polyhexamethyleneadipamide), PA 46 (polytetramethyleneadipamide), PA 610 (polyhexamethylenesebacamide), PA 69, PA 612, PA 46 and PA 1212, wherein the first number(s) always indicates the number of carbon atoms of the diamine followed by the number(s) indicating the number of carbon atoms of the dicarboxylic acid.

Polyamides are likewise obtainable by polycondensation from amino acid, for example $C_2$-$C_{20}$-amino acids, such as 6-aminocaproic acid or 11-aminoundecanoic acid, or by ring-opening polymerization from lactams, e.g. caprolactam. Examples of such polyamides are PA 4 (built up from 4-aminobutyric acid) and PA 6 (built up from 6-aminohexanoic acid). PA 11 is, for example, a polyundecanolactam and PA 12 is a polydodecanolactam. In the case of polyamides which are built up from only one monomer, as in this case, the number after the abbreviation PA indicates the number of carbon atoms of the monomer.

Polyamides can optionally be prepared with an elastomer as a modifying agent. Suitable copolyamides are, for example, block copolymers of the abovementioned polyamides with polyolefins, olefin copolymers, ionomers or chemically bonded or grafted elastomers; or with polyethers, for example with polyethylene glycol, polypropylene glycol or polytetramethylene glycol. Suitable polyamides or copolyamides are furthermore those modified with EPDM or ABS; and polyamides subjected to condensation during processing (RIM polyamide systems).

Polyamide is used in injection-molded parts with high requirements in respect of toughness, abrasion resistance and heat stability (dimensional stability), such as, for example, for structural components of plastic in the engine compartment of automobiles, toothed wheels, etc. Polyamide is moreover employed in synthetic fibers (e.g. nylon, Perlon).

In a preferred embodiment, the polyamide is a light- and heat stabilized polyamide. In another preferred embodiment, the polyamide is a polyamide of low viscosity. According to another preferred embodiment, the polyamide is a polyamide of high viscosity.

According to another preferred embodiment, the polyamide is a partially-aromatic copolyamide.

According to another preferred embodiment, the polyamide is one of the crystalline polyamide resins. A suitable polyamide of this type is e.g. derived from the polycondensation of m-xylylene diamine (MXDA) and adipic acid. Such a polyamide may also be used in combination with polyethylene terephthalate (PET), polypropylene (PP), or polyethylene (PE).

A further preferred embodiment of the present invention relates to a liquid composition, wherein the polymer is chosen from polymers which are derived from $\alpha,\beta$-unsaturated acids and derivatives thereof, such as polyacrylates and polymethacrylates; polymethyl methacrylates (PMMA), polyacrylamides (PAA) and polyacrylonitriles (PC), impact-modified with butyl acetate. As is known, polyacrylic acids are formed by polymerization of acrylic acid. The polymerization can be carried out as solution polymerization in water, as precipitation polymerization, for example in benzene, or as suspension polymerization.

Polyacrylic acid is employed in the form of its salts as a thickener and in aqueous media for coatings. Polyacrylic acid and its copolymers with acrylamide are used as suspending auxiliaries for pigments, as flocculating agents in water treatment, as drilling aids in mining, as paper auxiliaries, as an adhesive for metal/plastic bonds and for many other purposes. Polyacrylic acid esters are chiefly used as binders for paints and lacquers, in the paper industry in coating compositions and as binders and sizing agents, for finishing of textiles, in adhesives and sealing compositions, as leather auxiliaries, as elastomers and for many other purposes. A large field of use of PMMA is the use as a hardening component in binders of lacquer resins. In combination with acrylates, it produces high-quality coatings which are distinguished by their durability, film toughness, gloss and weather resistance. Such resins are employed in primers and coatings, and emulsion paints and lacquers. PAA is chiefly used as a flocculating agent in water treatment, as a paper auxiliary and as a flotation auxiliary in mining. It is moreover also employed as a clarifying aid for fruit juices, textile auxiliary, as a crosslinking agent in coatings, e.g. in the leather branch, as a thickener in emulsion paints, in adhesives and many other uses. Fields of use of PAC are knitted goods, home textiles (e.g. blankets, curtains, cushion fabrics) and carpets.

A further preferred embodiment of the present invention relates to a liquid composition, wherein the polymer is chosen from copolymers of the monomers mentioned in the above paragraph with one another or with other unsaturated monomers, such as acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

A further preferred embodiment of the present invention relates to a liquid composition, wherein the polymer is a copolymer of styrene with acrylonitrile and optionally additionally with butadiene and/or acrylic or methacrylic esters.

A further preferred embodiment of the present invention relates to a liquid composition, wherein the polymer is a polymer blend. The term "polymer blend" is understood as meaning a mixture of two or more polymers or copolymers. Polymer blends serve to improve the properties of the base component.

In a first particularly preferred embodiment, the polymer comprises at least one biopolymer. In this context, a biopolymer is understood as meaning a polymer of which the monomers at least partly occur in nature, e.g. carbohydrates and amino acids. Biopolymers of which the total structure occurs in nature are preferred. Examples of biopolymers are lignin, proteins, e.g. silk protein, gelatins, collagen, elastin and polysaccharides and modified polysaccharides, e.g. cellulose, cellulose derivatives, chitin, chitosan, dextran, hyaluronic acid, chondroitin sulfate, xylan and starch. Suitable cellulose derivatives are, for example, cellulose ester, such as cellulose acetates, cellulose propionates and cellulose butyrates, or the cellulose ethers, such as methylcellulose, ethyl cellulose, hydroxypropyl cellulose or carboxymethyl cellulose, silylated cellulose, etc. Cellulose is used, above all, in the clothing sector; and moreover as artificial silk, lining fabrics, curtain fabrics, tire cord, wadding, bandages and hygiene articles. Cellulose esters are processed, for example, to screwdriver handles, spectacles frames, brushes, combs, ballpoint pens, industrial parts, such as motor vehicle steering wheels, lighting and equipment covers, typewriter keys, electrical insulation films, films for photographic purposes and to light- and heat-resistant thermoplastic binders for lacquers. Cellulose ethers serve as binders for clear lacquer for textiles, paper, films and metals. Natural rubber (1,4-cis-polyisoprene) is indispensable for many uses, for example radial tires.

In a second particularly preferred embodiment, the polymer comprises at least one synthetic polymer. Especially preferred synthetic polymers are selected from polyurethanes, polyureas, polyamides and mixtures thereof. Further preferred synthetic polymers are selected from homopolymers and copolymers of cyclic ethers, polyamides, polysulfones and polyether sulfones.

A further preferred embodiment regards mixtures, comprising at least one biopolymer and at least one synthetic polymer. A particularly preferred embodiment regards mixtures, comprising cellulose or a cellulose derivative as biopolymer and at least one synthetic polymer selected from the group of homopolymers and copolymers of cyclic ethers, polyamides, polysulfones and polyether sulfones.

An especially preferred embodiment of the present invention regards mixtures, comprising cellulose and at least one polyamide. Another especially preferred embodiment of the present invention regards mixtures, comprising cellulose or a cellulose derivative and at least one polysulfone. Another especially preferred embodiment of the present invention regards mixtures, comprising cellulose or a cellulose derivative and at least one polyether sulfone. Another especially preferred embodiment of the present invention regards mixtures, comprising cellulose or a cellulose derivative and polytetramethylene ether glycol.

A further preferred embodiment regards mixtures, comprising as synthetic polymers at least one polyamide and polytetramethylene ether glycol. Another especially preferred embodiment of the present invention regards mixtures, comprising as synthetic polymers at least one polyamide and at least one polysulfone. Another especially preferred embodiment of the present invention regards mixtures, comprising as synthetic polymers at least one polyamide and at least one polyether sulfone.

Another especially preferred embodiment of the present invention regards mixtures, comprising as synthetic polymers at least one polysulfone and at least one polyether sulfone. Another especially preferred embodiment of the present invention regards mixtures, comprising as synthetic polymers at least one polysulfone and polytetramethylene ether glycol. Another especially preferred embodiment of the present invention regards mixtures, comprising as synthetic polymers at least one polyether sulfone and polytetramethylene ether glycol.

One especially preferred embodiment of the present invention relates to a liquid composition comprising
   at least one ionic liquid selected from the group consisting of
1,8-diazabicyclo[5.4.0]undec-7-enium formate,
1,8-diazabicyclo[5.4.0]undec-7-enium acetate,
1,8-diazabicyclo[5.4.0]undec-7-enium trifluoroacetate,
1,8-diazabicyclo[5.4.0]undec-7-enium tosylate,
1,8-diazabicyclo[5.4.0]undec-7-enium lactate,
1,8-diazabicyclo[5.4.0]undec-7-enium saccharinate,
1,8-diazabicyclo[5.4.0]undec-7-enium trifluoromethane sulfamate,
1,8-diazabicyclo[5.4.0]undec-7-enium methanesulfonate,
1,8-diazabicyclo[5.4.0]undec-7-enium hydrogensulfate,
1,8-diazabicyclo[5.4.0]undec-7-enium thiocyanate,
8-methyl-1,8-diazabicyclo[5.4.0]undec-7-enium hydrogensulfate,
8-methyl-1,8-diazabicyclo[5.4.0]undec-7-enium dimethylphosphate,
8-butyl-1,8-diazabicyclo[5.4.0]undec-7-enium chloride and
8-octyl-1,8-diazabicyclo[5.4.0]undec-7-enium chloride and
   at least one polymer selected from the group of cellulose, cellulose derivatives, homopolymers and copolymers of cyclic ethers, polyamides, polysulfones, polyether sulfones and mixtures thereof
solubilized therein.

In particular, the liquid composition according to the invention comprises as the polymer cellulose or a cellulose derivative. Suitable cellulose derivatives are e.g. methylcellulose, ethylcellulose, propylcellulose, hydroxyethylcellulose and hydroxypropylcellulose. Cellulose is used in particular. Any known form of cellulose can be employed as the cellulose, e.g. from wood fibers, linter fabric, pulp, cotton, cellulose obtained from paper, regenerated cellulose or bacterial cellulose.

Before the solubilization, the polymer is suitably subjected to mechanical comminution, e.g. by grinding and/or shredders. The solubilization is as a rule carried out by mixing the optionally previously comminuted polymer mechanically with the ionic liquid and stirring the mixture until solution is complete. In a particular embodiment of the invention, in order to accelerate the dissolving and homogenizing process the mixture is heated during or after the mixing, e.g. by microwave irradiation, but preferably not to a temperature of more than 180° C., preferably not more than 150° C., in particular not more than 120° C.

It has furthermore been found that the ionic liquids of the general formula I as defined above are particularly advantageously suitable for partial or complete solubilization of lignocellulose materials. In this context it is possible for at least one component of the lignocellulose material to be solubilized selectively or to be liberated selectively from a solubilized product which comprises several components of the lignocellulose material.

The invention therefore also relates to a process for selectively obtaining at least one constituent of a lignocellulose material, wherein the constituent is solubilized selectively and/or liberated selectively from a solubilized product of the lignocellulose material, and wherein at least one ionic liquid of the general formula I as defined above is employed for the solubilization.

In the context of the present invention, the term "selectively obtaining" is understood broadly. It includes obtaining in the pure or at least an enriched form. "Selectively obtaining" in the context of the invention therefore also exists if mixtures of the components wherein one component is enriched compared with the lignocellulose starting material are obtained. Preferably, at least one constituent of the lignocellulose material is obtained by the process according to the invention in a percentage amount which is at least 50%, particularly preferably at least 80% and at least 90% of the total amount of this constituent in the lignocellulose starting material.

Lignocellulose forms the structural matrix of the plant cell wall and comprises as main constituents lignin, hemicelluloses and cellulose. Lignin is a high molecular weight derivative of phenylpropane and has one or more methoxy groups on the phenyl rings and at least one hydroxyl group on the propyl units, depending on the natural source. Hemicelluloses or polyoses, like cellulose, are built up from glycosidically linked sugar units, but the chains are branched to a greater or lesser degree and the degree of polymerization is lower than in the case of cellulose (in general about 50 to 250).

The lignocellulose materials employed according to the invention are obtainable e.g. from wood and plant fibers as the starting substance. They are preferably cellulose-rich natural fiber materials, such as flax, hemp, sisal, jute, straw, coconut fibers and other natural fibers. Suitable lignocellulose materials are also obtained as a residue in agriculture and forestry, e.g. in the harvesting of cereals, maize, sugar cane etc.

Preferably, the process according to the invention comprises treatment of the lignocellulose material with at least one ionic liquid of the general formula I at a temperature of not more than 200° C., particularly preferably not more then 150° C. and in particular not more than 120° C. The treatment is preferably carried out at a temperature of at least 20° C., particularly preferably at least 40° C., in particular at least 60° C.

The pressure during the treatment of the lignocellulose material with at least one ionic liquid of the general formula I is in general in a range of from 0.1 bar to 100 bar, preferably 1 bar to 10 bar.

The duration of the treatment of the lignocellulose material with at least one ionic liquid of the general formula I is in general 1 minute to 10 days, preferably 30 minutes to 5 days.

In a first preferred embodiment, a liquid phase enriched in lignin and a residue enriched in cellulose is obtained in the treatment of the lignocellulose material with at least one ionic liquid of the general formula I. In this embodiment, at least one ionic liquid of the general formula I is employed for the treatment of the lignocellulose material, the anion being chosen from tosylate, trifluoroacetate, saccharinate, lactate, hydrogensulfate, trifluoromethanesulfonate, di(ethylhexyl) phosphate and thiocyanate.

In a second preferred embodiment, a liquid phase enriched in lignin and in cellulose is obtained in the treatment of the lignocellulose material with at least one ionic liquid of the general formula I and the liquid phase is subjected to a separation into a fraction enriched in lignin and a fraction enriched in cellulose. In this embodiment, at least one ionic liquid of the general formula I is employed for the treatment of the lignocellulose material, the anion being chosen from chloride, methanesulfonate, formate, acetate and di($C_1$-$C_4$-alkyl) phosphates. Suitable phosphates are dimethylphosphate and diethylphosphate.

Preferably, the separation into a fraction enriched in lignin and a fraction enriched in cellulose is carried out by addition of at least one further solvent to the ionic liquid. This can be a solvent which is not miscible with the ionic liquid or at least a solvent which has a miscibility gap with the ionic liquid, and is brought into intimate contact with the ionic liquid, a phase separation then being carried out to give a phase enriched in lignin and a phase enriched in cellulose. The solvent here can furthermore be a solvent which is at least partly miscible with the ionic liquid, and is brought into intimate contact with the ionic liquid, at least some of the lignin or cellulose being precipitated out.

Preferably, a solvent or solvent mixture which is chosen from water, alcohols, such as methanol, ethanol, n-propanol, isopropanol, n-butanol and tert-butanol, di- and polyols, such as ethanediol, propanediol and glycol, amino alcohols, such as ethanolamine, diethanolamine and triethanolamine, aromatic solvents, e.g. benzene, toluene, ethylbenzene or xylenes, halogenated solvents, e.g. methylene chloride, chloroform, carbon tetrachloride, dichloroethane or chlorobenzene, aliphatic solvents, e.g. pentane, hexane, heptane, octane, ligroin, petroleum ether, cyclohexane and decalin, ethers, e.g. tetrahydrofuran, diethyl ether, methyl tert-butyl ether and diethylene glycol monomethyl ether, ketones, such as acetone and methyl ethyl ketone, esters, e.g. ethyl acetate, formamide, dimethylformamide (DMF), dimethylacetamide, dimethylsulfoxide (DMSO) and mixtures thereof, is employed for the selective precipitation.

The aforementioned processes can be carried out continuously, discontinuously, or batch-wise.

It has furthermore been found that from liquid treatment media which contain ionic liquids of the general formula I, wherein the radical R represents hydrogen (i.e. the protonated amidine bases), the free bases can be isolated in the form of a separate phase if a base in a solvent (S1) comprising water and/or at least one water-miscible solvent) is employed for the deprotonation in an amount which simultaneously induces phase separation. Without being tied to a particular theory, this is presumably to be attributed to the increased dielectric constant and therefore the polarity of the aqueous phase compared with that of the phase containing the free amidine base. Alternatively to the addition of such a large amount of base in a solvent (S1), the phase separation can also be carried out by addition of an organic solvent (S2) which is not or at least not completely water-miscible. These solvents (S2) can also additionally be employed for addition of an amount of base in a solvent (S1) sufficient for inducing the phase separation. This then serves e.g. to accelerate the phase separation or to bring the enrichment of the free base in the non-aqueous phase to completion.

The invention also relates to a process for obtaining a base of the formula I.a

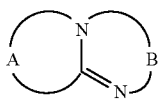

(I.a)

from a liquid treatment medium which comprises at least one ionic liquid of the general formula I

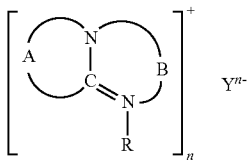

(I)

wherein the groups A and B are as defined before and R represents hydrogen, in which a solution of a suitable base (Bs) in a solvent (S1) comprising water an/or at least one water-miscible solvent is added to the liquid medium and a phase separation is induced to give a phase enriched in the base of the formula I.a.

The liquid treatment medium can be quite generally a spent treatment liquid, e.g. from a chemical or physical treatment process. In a preferred embodiment, the liquid treatment medium originates from one of the processes described above in which a liquid composition comprising at least one ionic liquid of the general formula I is employed for solubilization of at least one polymer. Specifically, the liquid treatment medium originates from one of the processes described above in which a liquid composition comprising at least one ionic liquid of the general formula I is employed for solubilization of cellulose or lignocelluloses.

The bases of the formula I.a can be converted back, optionally after working up, into ionic liquids of the general formula I. They can thus be recycled in an advantageous manner, and minimize losses. For working up, the bases can be subjected e.g. to a removal of the solvent and/or any impurities they still contain from the treatment processes in which they were employed.

The base (Bs) is preferably chosen from alkali metal and alkaline earth metal hydroxides, such as LiOH, NaOH, KOH, Ca(OH)$_2$ and Mg(OH)$_2$. The base (Bs) is preferably NaOH or KOH.

Preferably, the base (Bs) is employed in an amount of at least 2 molar equivalents, particularly preferably at least 3 molar equivalents, based on the content of the ionic liquid of the formula (I) in the liquid treatment medium.

Preferred solvents (S1) are aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of the dihydric alcohols, diethylene glycol, triethylene glycol, polyethylene glycols with number-average molecular weights up to about 3000, glycerol and dioxane. Particular preference is given to water/alcohol mixture, for example in a water/ethanol mixture.

Preferred organic solvents (S2) are, for example, aromatic solvents, e.g. toluene, ethylbenzene or xylene, halogenated solvents, e.g. methylene chloride, dichloroethane or chlorobenzene, aliphatic solvents, e.g. pentane, hexane or cyclohexane, and ethers, e.g. tetrahydrofuran, diethyl ether and methyl tert-butyl ether. They are particularly preferably ethers, and in particular methyl tert-butyl ether.

By the aforementioned process, the ionic liquid can be recycled or purified from substances therein.

A further object of the invention is to provide a process for preparing a compound of the formula I

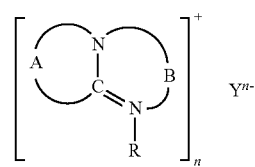

(I)

wherein

A together with the C—N group to which it is bonded, forms a 4- to 8-membered, saturated or unsaturated or aromatic ring, which is optionally substituted and/or which can optionally contain further heteroatoms or heteroatom-containing groups and/or which can include further fused-on saturated, unsaturated or aromatic carbocyclic rings or heterocyclic rings, B together with the amidino group to the nitrogen atoms of which it is bonded, forms a 4- to 8-membered, mono- or polyunsaturated, non-aromatic ring, which is optionally substituted and can include further fused-on saturated, unsaturated or aromatic carbocyclic rings or heterocyclic rings, R represents hydrogen, $Y^{n-}$ represents a mono-, di-, tri- or tetravalent anion, and n represents one, two, three or four, wherein a compound of the formula I.A

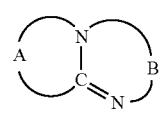

(I.A)

is reacted with an ammonium salt of the formula $(NH_4)_nY$.

The reaction of the amidine base of the formula (I) with an ammonium salt with liberation of ammonia can be carried out in an organic solvent. Suitable solvents are alcohols, such as methanol, ethanol, n-propanol, isopropanol, n-butanol and tert-butanol, ethers, e.g. diethyl ether and tetrahydrofurane, aromatic solvents, such as toluene, xylene or phenol, etc.

The molar ratio of compound (I) to ammonium salt is preferably 1:1 to 1:4, more preferably 1:1 to 1:2.

The reaction temperature is preferably from 0° C. up to 100° C., more preferably 10° C. to 60° C.

Ionic liquids of the general formula I can also be obtained by a solvent free process, wherein a compound of the formula I.A is reacted with an acid $H_nY$. In an alternative embodiment a solution of a compound of the formula I.A can be reacted with an acid $H_nY$ or a solution thereof. Preferred solvents are ethers, especially MTBE. Here the products separate from the solvent and can be isolated easily.

The reaction can be carried out under inert atmosphere, e.g. under nitrogen atmosphere.

The invention is explained in more details with the aid of the following, non-limiting examples.

EXAMPLES

Example 1

1,8-Diazabicyclo[5.4.0]undec-7-ene hydrochloride

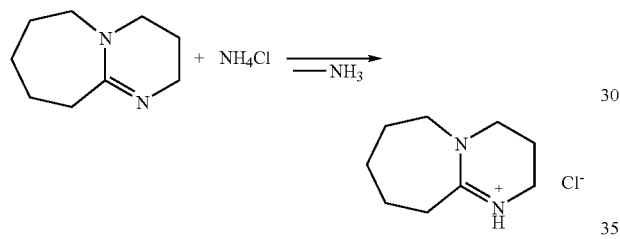

26.8 g (0.5 mol) of ammonium chloride were introduced into a 500 ml stirred reactor fitted with nitrogen inlet and separate feed device and suspended in 200 ml of methanol. Over the course of 30 minutes 76.1 g (0.5 mol) of 1,8-diazabicyclo[5.4.0]undec-7-ene (DBU) were added, where upon the reaction mixture was solubilized. The mixture was stirred for a further three hours and then the solvent was evaporated and the remaining solid dried in vacuo.

Example 2

1,8-Diazabicyclo[5.4.0]undec-7-enium thiocyanate

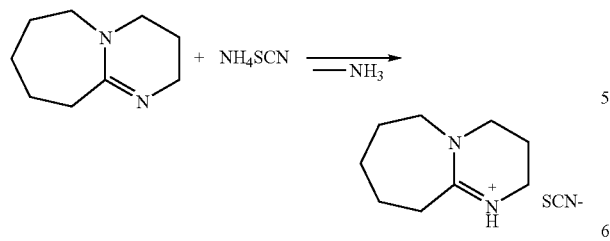

38.1 g (0.5 mol) of ammonium thiocyanate were introduced into a 500 ml stirred reactor fitted with nitrogen inlet and separate feed device and suspended in 200 ml of methanol. Over the course of 30 minutes 76.1 g (0.5 mol) of 1,8-diazabicyclo[5.4.0]undec-7-ene (DBU) were added, where upon the reaction mixture was solubilized. The mixture was stirred for a further three hours and then the solvent was evaporated and the remaining solid dried in vacuo.

Yield: 98.6%

Example 3

1,8-Diazabicyclo[5.4.0]undec-7-enium sulfamate

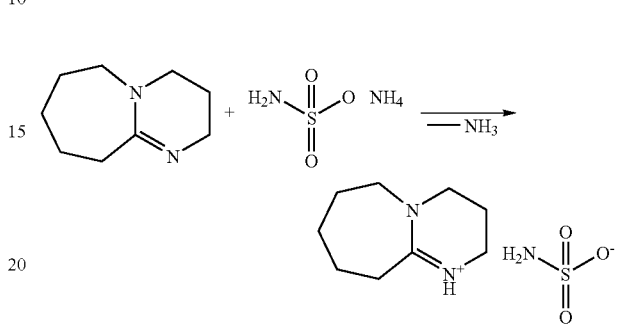

57.1 g (0.5 mol) of ammonium sulfamate were introduced into a 500 ml stirred reactor fitted with nitrogen inlet and separate feed device and suspended in 200 ml of methanol. Over the course of 30 minutes 76.1 g (0.5 mol) of 1,8-diazabicyclo[5.4.0]undec-7-ene (DBU) were added, where upon the reaction mixture was solubilized. The mixture was stirred over night at ambient temperature and then the solvent was evaporated and the remaining solid dried in vacuo.

Yield: 99%

Example 4

Solubility of Lignocellulose Materials in Ionic Liquids of the DBU Type

According to a general procedure a wood sample (aspen wood, chips or powder, no further pretreatment), a cellulose sample and a sulfur free lignin sample, each of 140 mg (5% by weight with regard to the employed ionic liquid) were stirred in 7 g of a molten ionic liquid at an increased temperature under a flow of inert gas. The obtained solutions and residues (if present) were analyzed with regard of their content of lignin and cellulose. If the obtained solutions from wood contained lignin and cellulose, a further solvent was added to effect precipitation of the cellulose. The results are shown in table 1. The following solvents were employed for the precipitation of the cellulose:

1) water
2) methanol
3) ethanol
4) isopropanol
5) acetone
6) methylene chloride
7) chloroform
8) acetonitril
9) tetrahydrofuran

TABLE 1

| Ionic liquid | Temperature/time | Result | Solvent(s) used for precipitation |
|---|---|---|---|
| DBU[#] chloride | 150° C./1 day | wood completely dissolved; lignin and cellulose dissolved | 1, 2, 3, 4, 6, 7, 8 |
| DBU[#] methanesulfonate | 100° C./3 days | lignin and cellulose dissolved | 1, 2, 3, 4, 6, 7, 8 |
| DBU[#] formate | 100° C./1 day | wood almost completely dissolved; lignin and cellulose dissolved | 1, 2, 3, 4, 6, 8 |
| DBU[#] acetate | 100° C./1 day | wood partly dissolved; lignin and cellulose dissolved | 1, 5, 8 |
| 8-Butyl-DBU chloride | 100° C./2 days | wood partly dissolved; lignin and cellulose dissolved | 1, 2, 3, 4, 5, 6, 8 |
| 8-Octyl-DBU chloride | 100° C./2 days | wood partly dissolved; lignin and cellulose dissolved | 2, 3, 4, 5, 6, 7, 8, 9 |
| DBU[#] tosylate *) | 100° C./4 days | lignin dissolved | — |
| DBU[#] trifluoroacetate | 100° C./2 days | lignin dissolved | — |
| DBU[#] saccharinate | 120° C./1 day | lignin dissolved | — |
| DBU[#] hydrogensulfate | 100° C./2 days | lignin dissolved | — |
| DBU[#] lactate | 50° C./4 days | lignin dissolved | — |
| DBU[#] thiocyanate *) | 100° C./1 day | lignin dissolved | — |
| DBU[#] trifluoromethane sulfamate | 100° C./1 day | lignin dissolved | — |

DBU[#] = protonated DBU
*) wood is delignified

Example 5

Solubility of the Polymer Material in Ionic Liquids of the DBU Type

According to a general procedure a polymer material sample each of 5 g (in form of chips, if not specified otherwise) were dissolved in 95 g of the ionic liquid specified in table 2. The reaction conditions are specified in table 2. Abbreviations:

| | |
|---|---|
| DBU SCN | 1,8-diazabicyclo[5.4.0]undec-7-enium thiocyanate |
| DBU HSO$_4$ | 1,8-diazabicyclo[5.4.0]undec-7-enium hydrogen sulfate |
| DBU acetate | 1,8-diazabicyclo[5.4.0]undec-7-enium acetate |
| MeDBU Me$_2$PO$_4$ | 8-methyl-1,8-diazabicyclo[5.4.0]undec-7-enium dimethylphoshate |
| polyTHF ® | available from BASF, Germany |
| MXD6 | Nylon-MXD6, available from Mitsubishi Gas Chemical Company, Inc. |
| Ultrason ® E | available from BASF AG, Germany |
| Ultrason ® S | available from BASF AG, Germany |
| Ultramid ® A27 | unreinforced PA 66 grade, low viscosity, available from BASF AG, Germany |
| Ultramid ® B5 | unreinforced PA6, high viscosity, available from BASF AG, Germany |
| Ultramid ® B24N | unreinforced PA6, low viscosity, available from BASF AG, Germany |
| Ultramid ® TKR | partly aromatic copolyamides (PA6/6T), base: caprolactam, hexamethylenediamine and terepthalic acid, available from BASF AG, Germany, |
| Ultramid ® T315 | partially-aromatic copolyamide (PA6/6T), base: caprolactam, hexamethylenediamine and terepthalic acid, available from BASF AG, Germany, |

TABLE 2

| Ionic liquid | Polymer | trade-name | Temp. [° C.] | Time | Amount dissolved [%] | Result |
|---|---|---|---|---|---|---|
| DBU SCN | polytetramethylene ether glycol | polyTHF ® | 100 | 5 h | 5 | dissolved |
| DBU HSO$_4$ | polytetramethylene ether glycol | polyTHF ® | 100 | 21 h | 5 | dissolved |
| DBU HSO$_4$ | polyamide | MXD6 | 150 | 23 h | 5 | dissolved |
| MeDBU Me$_2$PO$_4$ | polysulfone | Ultrason ® E | 90 | 23 h | 10 | dissolved |
| MeDBU Me$_2$PO$_4$ | polysulfone | Ultrason ® E | 90 | 28.5 h | 15 | dissolved |
| MeDBU Me$_2$PO$_4$ | polyamide | Ultramid ® B5 | 90 | 18 h | 5 | dissolved |
| MeDBU Me$_2$PO$_4$ | polyamide | Ultramid ® B5 | 100 | 3 d | 20 | dissolved |
| MeDBU Me$_2$PO$_4$ | polyamide | Ulramid ® T315 | 90 | 18 h | 5 | dissolved |
| MeDBU Me$_2$PO$_4$ | polyamide | Ulramid ® T315 | 100 | 4 d | 25 | dissolved |
| MeDBU Me$_2$PO$_4$ | polyamide | Ultramid ® A 27 | 90 | 22.5 h | 5 | dissolved |
| MeDBU Me$_2$PO$_4$ | polyamide | Ultramid ® A 27 | 100 | 1.5 h | 15 | dissolved |
| MeDBU Me$_2$PO$_4$ | polyamide | Ultramid ® B24N | 90 | 18 h | 5 | dissolved |
| MeDBU Me$_2$PO$_4$ | polyamide | Ultramid ® B24N | 90 | 3 d | 15 | dissolved |
| MeDBU Me$_2$PO$_4$ | polyamide | Ultramid ® B24N, powder | 90 | 18 h | 5 | dissolved |

TABLE 2-continued

| Ionic liquid | Polymer | trade-name | Temp. [° C.] | Time | Amount dissolved [%] | Result |
|---|---|---|---|---|---|---|
| MeDBU Me$_2$PO$_4$ | polyamide | Ultramid ® B24N, powder | 90 | 2 d | 25 | dissolved |
| MeDBU Me$_2$PO$_4$ | polyamide, PA6 | — | 90 | 22.5 h | 5 | dissolved |
| MeDBU Me$_2$PO$_4$ | polyamide, PA6 | — | 100 | 3.5 d | 20 | dissolved |
| MeDBU Me$_2$PO$_4$ | polysulfone | Ultrason ® E, powder | 90 | 18 h | 5 | dissolved |
| MeDBU Me$_2$PO$_4$ | polysulfone | Ultrason ® E, powder | 90 | 2 d | 20 | dissolved |
| MeDBU Me$_2$PO$_4$ | polyamide | Ultramid ® TKR | 90 | 22.5 h | 5 | dissolved |
| MeDBU Me$_2$PO$_4$ | polyamide | Ultramid ® TKR | 90 | 3 d | 30 | dissolved |
| MeDBU Me$_2$PO$_4$ | polyamide | MXD6 | 90 | 18 h | 5 | dissolved |
| MeDBU Me$_2$PO$_4$ | polyamide | MXD6 | 90 | 3 d | 30 | dissolved |
| MeDBU Me$_2$PO$_4$ | cellulose | — | 100 | 24 h | 10 | dissolved |
| DBU acetate | polyamide | MXD6 | 100 | 4 h | 30 | dissolved |
| DBU acetate | polyamide, PA6 | — | 100 | 2.5 h | 15 | dissolved |
| DBU acetate | polysulfone | Ultrason ® E, powder | 100 | 24 h | 25 | dissolved |
| DBU acetate | cellulose, powder | — | 100 | 24 h | 10 | dissolved |

We claim:

1. A process for obtaining at least one constituent of a lignocellulose material, wherein the constituent is solubilized selectively, or liberated selectively or solubilized and liberated selectively from a solubilized product of the lignocellulose material, and wherein at least one ionic liquid is employed for the solubilization and/or liberation, wherein the at least one ionic liquid is at least one ionic liquid represented by formula I

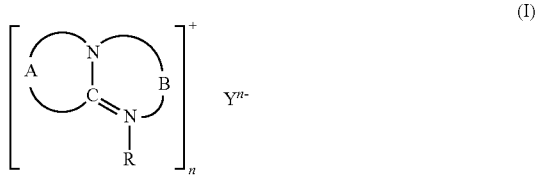

wherein
A together with the C—N group to which it is bonded, forms a 4- to 8-membered, saturated or unsaturated or aromatic ring, which is optionally substituted, which can optionally have further heteroatoms or heteroatom-containing groups, and which can have further fused-on saturated, unsaturated or aromatic carbocyclic rings or heterocyclic rings,
B together with the amidino group to which it is bonded, forms a 4- to 8-membered, mono- or polyunsaturated, non-aromatic ring, which is optionally substituted and can have further fused-on saturated, unsaturated or aromatic carbocyclic rings or heterocyclic rings,
R represents hydrogen or an organyl radical,
Y$^{n-}$ represents a mono-, di-, tri- or tetravalent anion, and n represents one, two, three or four
and at least one polymer solubilized therein.

2. The process according to claim 1, comprising obtaining a liquid phase enriched in lignin and a residue enriched in cellulose by treating the lignocellulose material with at least one ionic liquid of the general formula I.

3. The process according to claim 2, comprising employing at least one ionic liquid of the general formula I for treating the lignocellulose material, wherein the anion is selected from the group consisting of tosylate, trifluoroacetate, saccharinate, lactate, hydrogensulfate, trifluoromethanesulfonate, di(ethylhexyl)phosphate and thiocyanate.

4. The process according to claim 1, comprising obtaining a liquid phase enriched in lignin and in cellulose by treating the lignocellulose material with at least one ionic liquid of the general formula I, and separating the liquid phase into a fraction enriched in lignin and a fraction enriched in cellulose.

5. The process according to claim 4, employing at least one ionic liquid of the general formula I for treating the lignocellulose material, wherein the anion is selected from the group consisting of chloride, methanesulfonate, formate, acetate and a di(C$_1$-C$_4$-alkyl)phosphate.

6. The process of claim 1, wherein in the formula I the cations are selected from the group consisting of cations of formulae I.1 and I.2

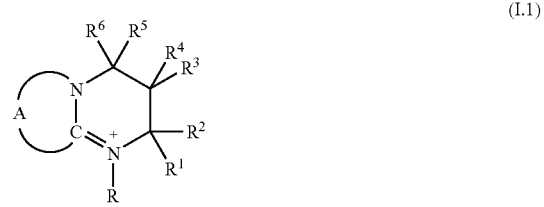

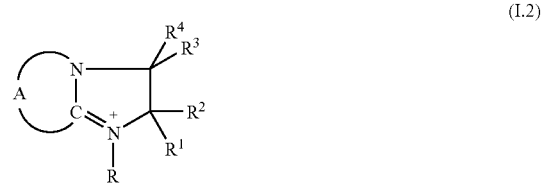

wherein
R and A are defined according to claim 1, and
R$^1$, R$^2$, R$^3$, R$^4$, R$^5$ and R$^6$ independently of one another represent hydrogen, alkyl, alkenyl, cycloalkyl, cycloalkenyl, polycyclyl, heterocycloalkyl, aryl, hetaryl, hydroxyl, SH, polyalkylene oxide, polyalkyleneimine, alkoxy, alkylthio, alkylsulfinyl, alkylsulfonyl, halogen, SO$_3$H, sulfonate, NE$^1$E$^2$, nitro, alkoxycarbonyl, COOH, carboxylate, formyl, acyl or cyano, wherein E$^1$ and E$^2$ denote in each case identical or different radicals selected from the group consisting of hydrogen, alkyl, cycloalkyl and aryl,
wherein the radicals R$^1$, R$^2$, R$^3$, R$^4$, R$^5$ and R$^6$ which represent alkyl radicals can have 1, 2, 3, 4 or 5 substituents selected from the group consisting of cycloalkyl, heterocycloalkyl, aryl, hetaryl, cycloalkoxy, cycloalkylthio, heterocycloalkoxy, heterocycloalkylthio, aryloxy, arylthio, hetaryloxy, hetarylthio, hydroxyl, SH, COOH, carboxylate, $SO_3H$, sulfonate, $NE^4E^5$, $(NE^4E^5E^6)^+X^-$, halogen, nitro, formyl, acyl and cyano, wherein $E^4$, $E^5$ and $E^6$ denote in each case identical or different radicals selected from the group consisting of hydrogen, alkyl, cycloalkyl and aryl and $X^-$ represents an anion equivalent, and wherein the radicals $R^1$, $R^2$, $R^3$, $R^4$, $R^5$ and $R^6$ which represent cycloalkyl, cycloalkenyl, polycyclyl, heterocycloalkyl, aryl and hetaryl radicals can have 1, 2, 3, 4 or 5 substituents which are selected from the group consisting of alkyl and the substituents for the alkyl radicals $R^1$ to $R^6$, or $R^1$ and $R^3$, if present, $R^4$ and $R^6$ or a combination thereof, together with the ring carbons to which they are bonded, represent a 5- to 8-membered saturated, unsaturated or aromatic carbo- or heterocyclic radical, which is optionally and additionally fused with one, two or three cycloalkyl, heterocycloalkyl, aryl or hetaryl, wherein the carbo- or heterocyclic radical and, if present, the fused-on groups independently of one another can each carry one, two, three or four substituents which are selected from the group consisting of alkyl, cycloalkyl, heterocycloalkyl, aryl, hetaryl, hydroxyl, SH, halogen, COOH, carboxylate, $SO_3H$, sulfonate, $NE^7E^8$, $(NE^7E^8E^9)^+X^-$, nitro, alkoxycarbonyl, formyl, acyl and cyano, wherein $E^7$, $E^8$ and $E^9$ denote in each case identical or different radicals selected from the group consisting of hydrogen, alkyl, cycloalkyl and aryl and $X^-$ represents an anion equivalent, wherein in the formula I.1, $R^1$ and $R^3$ or $R^3$ and $R^5$ also together can represent the bond portion of a double bond between the ring atoms which carry these radicals.

7. The process of claim 1, wherein in formula I, A, together with the C—N group to which it is bonded, represents a 5- to 8-membered ring which is optionally and additionally fused with one, two or three cycloalkyl, cycloalkenyl, heterocycloalkyl, aryl or hetaryl, wherein the heterocyclic radical and, if present, the fused-on groups independently of one another can each carry one, two, three or four substituents which are selected from the group consisting of alkyl, alkenyl, cycloalkyl, cycloalkenyl, heterocycloalkyl, aryl, hetaryl, hydroxyl, SH, polyalkylene oxide, polyalkyleneimine, alkoxy, halogen, COOH, carboxylate, $SO_3H$, sulfonate, $NE^{10}E^{11}$, $(NE^{10}E^{11}E^{12})^+X^-$, nitro, alkoxycarbonyl, formyl, acyl and cyano, wherein $E^{10}$, $E^{11}$ and $E^{12}$ denote in each case identical or different radicals selected from the group consisting of hydrogen, alkyl, cycloalkyl and aryl and $X^-$ represents an anion equivalent.

8. The process of claim 1, wherein in the formula I the cations are selected from the group consisting of cations of 1,5-diazabicyclo[4.3.0]non-5-ene and 1,8-diazabicyclo[5.4.0]undec-7-ene.

9. The process of claim 1, wherein the polymer comprises at least one biopolymer.

10. The process of claim 1, wherein the polymer is a polysaccharide or a modified polysaccharide.

11. The process of claim 1, wherein the polymer is cellulose.

12. The process of claim 1, wherein the polymer comprises at least one synthetic polymer.

13. The process of claim 1, wherein the polymer is selected from the group consisting of a polyurethane, a polyurea, a polyamide, a polysulfone, a polyether sulfone, a homopolymer and a copolymer of cyclic ether, or mixtures thereof.

14. The process of claim 1, wherein the polymer comprises cellulose and at least one synthetic polymer selected from the group consisting of a polyurethane, a polyurea, a polyamide, a polysulfone, a polyether sulfone, homopolymer and a copolymer of cyclic ether and mixtures thereof.

15. A liquid composition obtained by the process of claim 1.

* * * * *